US006534101B1

(12) United States Patent
Sabatier et al.

(10) Patent No.: US 6,534,101 B1
(45) Date of Patent: Mar. 18, 2003

(54) ENZYMES MIXTURE OBTAINED FROM *PENICILLIUM FUNICULOSUM*

(75) Inventors: Alain Sabatier, Paris (FR); Neville Marshall Fish, Bramhall (GB); Nigel Paterson Haigh, Huddersfield (GB)

(73) Assignee: Aveatis Animal Nutrition S.A., Anthony (FR)

(*) Notice: Subject to any disclaimer, the term of this patent is extended or adjusted under 35 U.S.C. 154(b) by 0 days.

(21) Appl. No.: 09/462,246

(22) PCT Filed: May 6, 1999

(86) PCT No.: PCT/IB99/00856

§ 371 (c)(1), (2), (4) Date: Apr. 7, 2000

(87) PCT Pub. No.: WO99/57325

PCT Pub. Date: Nov. 11, 1999

(30) Foreign Application Priority Data

Sep. 19, 2001 (EP) .......................................... 98401101

(51) Int. Cl.$^7$ ............................ A23B 7/10; C12N 1/14; C12N 9/00; C12N 9/30; C12N 9/42; C12N 9/18

(52) U.S. Cl. ..................... 426/53; 435/254.5; 435/183; 435/203; 435/209; 435/197; 435/256.3; 426/656; 426/18; 426/44

(58) Field of Search ................................ 435/183, 209, 435/200, 254.5, 203, 197, 256.3; 426/656, 18, 44, 53

(56) References Cited

U.S. PATENT DOCUMENTS 5,720,971 A 2/1998 Beauchemin et al. ....... 424/438

FOREIGN PATENT DOCUMENTS

| | | |
|---|---|---|
| DE | 1945147 | 5/1970 |
| GB | 2286396 | 8/1995 |
| GB | 2301103 | 11/1996 |
| WO | 9605739 | 2/1996 |

OTHER PUBLICATIONS

Lachke et al., "Isolation of a hypercelulolytic mutant (Cu–1) of Penicillium funiculosum", *Enzyme Microb. Technol.*, vol. 8, Feb. 1986, pp. 105–108.

Ralet et al., "Degradation of feruloylated oligosaccharides from sugar–beet pulp and wheat ran by ferulic acid esterases from Aspergillus niger", *Carbohyrate Research* 263 (1994), pp. 257–269.

English Abstract JP 7090300, DERWENT Publication, AN 95–167488, ORD Apr. 4, 1995, 1 page.

*Primary Examiner*—Rebecca E. Prouty
*Assistant Examiner*—David J. Steadman
(74) *Attorney, Agent, or Firm*—Baker Botts LLP

(57) ABSTRACT

The present invention relates to a novel micro-organism, *Penicillium funiculosum*, to a new enzymes mixture obtained from it, and nucleic acid sequences encoding such enzymes.

18 Claims, 5 Drawing Sheets catccatacaggtttctcctgtatggaatttgtaattacttatcactaattgtcacaattctcaggttttctgaacatgc tttcttttccgtccggcattgttaagcttgatcatagcctgtgtttcttaaaggcggttccggcggtaatctcagtacta cgtcctacgtatgtaggtagttatatctatcctaccctttgactgtatgttccctactttgcagtacttagacaacgatt ttctaggcaggttcctagaatgctctcgttttcgtttactatcattgtttttatgcgcgtaatgtggagctattgacgtg tatgtcactttacatgcctataactaacttaatctaaacgtccattaggggttcaacatatgtattccccgcctccgcat gttcactccaatgtggaaattatctccaccgtgcccaacacttccctgataatgagcaatgtcgatgagtatttcaatgc aagaatctgagccgaatcaagttttacaaggttagtcattggttgatcctgttgtcgaaagctagtgcaggttatgctcc gccgatgaa<u>ggctaaa</u>tatataacgggagataaccctaactacctaggtatcaacccaacgcgacattgaaaatcttca aaaacatccttactagcggatatcaatagcgagaactgcgattaaacattgtcgatcttcggcactttagcagcatgact tca<u>ggctaaa</u>cacattgatgcaaaccgctttctcattttacctgaaacttgggatgacgaatcctccaaccagttgtcga aacgaacaggctccacatctcgcaacaaatcaaagcaacgagtctaatatatgtattcgtcatctagtaaagatcaaacg atttcgtttcagcggtggtacataccccaagcactccgacaagtcggttatccagacctgtcgatcttgaatatcgccca tacagagctcttctttaaagaccacgaccgaacatcaaggagaatttagccagaaattttccggtatgcgagaatgatcc cagatttgcaacagaaaagtgctctattgcgaatatcctcaagcatattccccgaaactccgcgatggagaccttgaggg gggtcatatggatgcgaggcatgatgaaacaaacaacccgttactgttaaatgagaaatgagaatgcgggtatataaac atgcggattgtcctcgccagaaatccccccccccccccccaccaaaacaaaagacgtaccactcatttctggatatc cacacttggcgagaatcaaagaaccatttcaatcaag ATG AAG CTC TTC CTA GCT GCA ATT
M K L F L A A I GTC CTT TGC GCA ACT GCC GCG ACA GCC TTC CCA TCA GAA CTT GCT CAA CGC GCT GCG GGA
V L C A T A A T A F P S E L A Q R A A G GAC CTT AGC AAG CGT CAA TCA ATC ACG ACC AGC CAG ACT GGG ACG AAC AAC GGC TAC TAC
D L S K R Q S I T T S Q T G T N N G Y Y TAC TCG TTC TGG ACC AAC GGC GGA GGA GAA GTC ACT TAC ACA AAT GGC GAC AAT GGC GAG
Y S F W T N G G G E V T Y T N G D N G E TAC AGC GTG ACA TGG GTC GAT TGT GGT GAC TTT ACA TCT GGC AAG GGC TGG AAT CCA GCC
Y S V T W V D C G D F T S G K G W N P A AAT GCA CA <u>gtaagt</u>ttccctctttccttctaagcttatattgtacgtactcacaatttg<u>cag</u> G ACT GTC ACG
N A Q T V T TAC TCA GGA GAA TTT AAC CCC TCT GGA AAC GCT TAT TTG GCT GTC TAC GGG TGG ACA ACA
Y S G E F N P S G N A Y L A V Y G W T T

Figure 1

```
GAT CCT CTT GTC GAA TAC TAC ATC CTG GAG TCC TAC GGC ACC TAT AAC CCA TCA TCT GGA
D   P   L   V   E   Y   Y   I   L   E   S   Y   G   T   Y   N   P   S   S   G

CTT ACT TCA CTT GGC CAG GTC ACT AGC GAT GGT GGC ACC TAC GAT ATC TAC TCA ACC CAG
L   T   S   L   G   Q   V   T   S   D   G   G   T   Y   D   I   Y   S   T   Q

CGT GTC AAC CAG CCT TCC ATT GAG GGA ACT TCC ACC TTC AAC CAG TAC TGG TCA GTT CGC
R   V   N   Q   P   S   I   E   G   T   S   T   F   N   Q   Y   W   S   V   R

ACC GAG AAG CGA GTC GGC GGA ACT GTC ACC ACG GCC AAC CAC TTT GCA GCA TGG AAG GCA
T   E   K   R   V   G   G   T   V   T   T   A   N   H   F   A   A   W   K   A

CTT GGA CTT GAA ATG GGC ACT TAT AAC TAT ATG ATT GTG TCC ACC GAA GGC TAC GAG AGC
L   G   L   E   M   G   T   Y   N   Y   M   I   V   S   T   E   G   Y   E   S

AGT GGC TCT AGT ACC ATC ACA GTG TCC TAG acatgtctcaatgacgcttgttacacagctgtccctttat
S   G   S   S   T   I   T   V   S   Z

tgacacttataaatgacttatggaagggagtcggcaaaatttttatgttcgaagtttcatatgtctattgtggaaatcggccc

atattttcagggctagtcactctttgattgcatcttaagttacttgatcaaattaagccctaacaccaagatctggaatgcga

gcaatatcaagtatttattcatttattttaaaccccggagtgggctgtctttgatagtatagtaatgatgcacatttgttgtg

gcagccttacctgtttttccattggcattcgagatatctaccgacatgttccttcagcaagcagtatttatcgcgtctcgatc

aagcatcgacggccttttggggaaaccaagaaaaatatttggcctccatatctctgtcgcacattccctccttctctgaaac

ctttgcttttgggaacgttcgaaaaaacagagcggttgcaagcagtagctccatccaggcaagatgcataccgatgcatacta

gtgagtaggccagttagcgaattgtttgttctcagtgccgatgatgaaattatgcaattaaagacttactgcgagacccgcca

ccaaagggcatgaaaacatgcttcatctcttttgtgggattctcccatctgcttggatcaaagctatatcccggacatcaata

gttagcgatattgaatcgaacatctgccatgccttgtaggcgggaaagtgacaccgaataggctataggaaccactcacgcat

gaggattgggaaacacatcagggtcgcgatgtaaagtatatgcctgagtagatactgtgacacctccag
```

Figure 1 (continued)

| | | | | | | | | | | | | | | |
|---|---|---|---|---|---|---|---|---|---|---|---|---|---|---|
| GCC | AAG | TAC | GGT | ACG | GGT | TAT | TGT | GAC | TCT | CAA | TGC | CCT | CGT | GAC |
| A | K | Y | G | T | G | Y | C | D | S | Q | C | P | R | D |
| TTG | AAG | TTC | ATC | GCT | GGT | CAG | GCC | AAC | GTC | GAG | GGC | TGG | ACG | CCT |
| L | K | F | I | A | G | Q | A | N | V | E | G | W | T | P |
| TCC | ACC | AAC | AAC | TCG | AAC | ACT | GGA | ATC | GGC | AAC | CAC | GGA | TCT | TGC |
| S | T | N | N | S | N | T | G | I | G | N | H | G | S | C |
| TGC | GCG | GAG | CTT | GAT | ATC | TGG | GAA | GCA | AAC | AGT | ATC | TCA | GAG | GCC |
| C | A | E | L | D | I | W | E | A | N | S | I | S | E | A |
| TTG | ACT | CCT | CAC | CCT | TGC | GAT | ACA | CCC | GGC | CTA | ACT | GTT | TGC | ACT |
| L | T | P | H | P | C | D | T | P | G | L | T | V | C | T |
| GCT | GAT | GAC | TGT | GGT | GGT | ACC | TAC | AGC | TCC | AAT | CGT | TAT | GCC | GGT |
| A | D | D | C | G | G | T | Y | S | S | N | R | Y | A | G |
| ACT | TGC | GAC | CCC | GAT | | | | | | | | | | |
| T | C | D | P | D | | | | | | | | | | |

Figure 2

CCG GGT ACT CAA CCT GTG GCA TAC TAC GGA CAG CAT GGT GTG AGT

P G T Q P V A Y Y G Q H G V S

GAT ACG GTA CTG CCT TTC TCA TTG GGA GAA GGG ATT AGG GAT ACG

D T V L P F S L G E G I R D T

TTT GTC AAG GAT GAT CAT TGT ACA CCG ACA AAC CCG CCC GCC CCT

F V K D D H C T P T N P P A P

GCT GCT GGA AGT GGA ACC CAC ATC AAG TAT GTA

A A G S G T H I K Y V

Figure 3 maiplvlvlawllpvvlaASLTQVNNFGDNPGSLQMYIYVPNKLASKPAIIVAMHPCGGSATE

YYGMYDYHSPADQYGYILIYPSATRDYNCFDAYSSASLTHNGGSDSLSIVNMVKYVISTYGAD

SSKVYMTGSSSGAIMTNVLAGAYPDVFAAGSAFSGMPYACLYGAGAADPIMSNQTCSQGQIQH

TGQQWAAYVHNGYPGYTGQYPRLQMWHGTADNVISYADLGQEISQWTTIMGLSFTGNQTNTPL

SGYTKMVYGDGSKFQAYSAAGVGHFVPTDVSVVLDWFGITSGTTTTTTPTTTPTTSTSPSSTG

GCTAAHWAQCGGIGYSGCTACASPYTCQKANDYYSQCL

Figure 4

ENZYMES MIXTURE OBTAINED FROM *PENICILLIUM FUNICULOSUM*

FIELD OF THE INVENTION

The present invention relates to a novel micro-organism, new enzymes and new enzymes mixture. In addition, the present invention relates to the composition of the enzymes mixture, its preparation and its use in feed, food and other industries including but not limited to the paper industry and the textile industry.

BACKGROUND OF THE INVENTION

Enzymes have been used for a long time for a variety of different industrial applications. Examples are known in the baking industry, in the wine and fruit juices industry (where enzymes are used to breakdown pectins and β-glucans), in the textile industry (where cellulases are used to obtain soft and smooth cellulosic fabrics) and also, which is not the least application, for animal feed. In this case the enzymes improve the digestibility of vegetable sources.

This last use enables the livestock to digest feed more efficiently. The value of a feed can be measured by the FCR (Feed Conversion Ratio), a nutritive ratio of the amount of feed consumed relative to the weight gain of the animal. A decrease in FCR, for a feed, indicates the animal gains proportionately more weight for a given quantity of feed ; i.e. the animal is able to utilize the feed more efficiently.

Poor digestibility of the feed components (starch, fat, protein/amino acids) is a noted feature of cereal-based feeds and, for example, particularly those containing a high barley or wheat content. In these cases it may be necessary to formulate the teed to contain higher levels of energy from other sources and other supplements such as amino acids. These enzymes increase the Apparent Metabolizable Energy value of the cereals incorporated into the Feed.

Another approach to resolve this problem has been to add enzyme supplements, cellulases, endo-1,3(4)-β-glucanases (β-glucanases), endo-1,4-β-xylanases (xylanases) etc., or mixtures of enzyme activities, to these cereal-based feeds. Enzyme supplements may have a specific use to hydrolyze the β-glucans, or to hydrolyze the arabinoxylans, found in the cereals (typically barley and wheat). The addition of enzymes has differents goals. One advantage which clearly proves the efficacy of feed enzyme supplements is the reduction in viscosity of materials in the gut of the animals which receive cereal-based feed containing the appropriate enzyme supplement. The higher viscosity is due, in part, to β-glucans and arabinoxylans found in barley and wheat. The lower viscosity, resulting from enzyme action, permits an easier absorption of nutritional components in the animal's gut. The other advantage is the release of nutrients entrapped by the cell walls of the cereals decreasing the requirement for other costly feed supplements. Overall the result is a significant reduction in the cost of the feed with a similar or beneficial effect as measured by the FCR.

Enzymes preparations originating from a range of different micro-organisms have been described to improve feed digestibility.

If we consider prior art related to the use of enzymes in the animal feed we can mention the European Patent No 0.699.762 which describes use of a phytase issued from *Schwanniomyces occidentalis*. This phytase is a phytase obtained from genetically modified organism obtained by including cloned gene that we would like to avoid in the present invention.

If we consider the WO 95/26398 patent application, again a modified cellulase is obtained by inclusion of foreign DNA sequence in an host cell which modifies the nature of the original strain which is chosen in the following list of micro-organisms: Bacillus, Streptomyces, Saccharomyces, Schizosaccharomyces, Aspergillus. In the present invention our main aim was to avoid foreign gene inclusion in the micro-organism which is the producer of the enzyme.

In the WO 96/05739 patent application, a mixture of enzymes (xylanase, protease and, optionally, β-glucanase) is obtained from different micro-organisms. The authors give example (page 5) of enzymes mixture with a ratio of xylanase activity to β-glucanase activity of the order of 1:5. It has been found that when a xylanase is included in a cereal-based diet at or around its optimum dosage level, the co-presence of enzymes possessing β-glucanase activity increase the FCR of the feed which is of course disadvantageous. Consequently the authors advise against the presence of β-glucanase, they recommend a maximum ratio of xylanase activity to β-glucanase activity of 1:0–0.25.

In some cases, in order to ensure all the enzyme activities relevant to the feed application are present, preparations are made up from preparations from more than one micro-organism. In a number of cases the enzyme preparations have been obtained from microorganisms subjected to genetic modification using recombinant DNA techniques.

We have discovered and developed a new micro-organism belonging to the class of *Penicillium funiculosum*, that contains new enzymes and a mixture of enzyme activities which can be used successfully to increase mainly the digestibility of cereal-based animal feeds.

SUMMARY OF THE INVENTION

Accordingly, the present invention relates to a new micro-organism derived from *Penicillium funiculosum* and a method for cultivating this micro-organism and for recovering the enzymes produced by this micro-organism.

In addition, in accordance with this invention, there are provided new enzymes issued from this micro-organism, nucleic acid sequences therefrom and new compositions containing those enzymes.

Further, in accordance with this invention, there is provided a method for improving the digestibility of aminoacids and cereal-based animal feeds and amino acids.

Another subject of the present invention is the reduction of phosphorus excretion and ammonia excretion from the battery where animals are fed.

DETAILED DESCRIPTION OF THE INVENTION

A. The New Strain *Penicillium funiculosum*

This new strain of the fungus *Penicillium funiculosum* is deposited under the number IMI 378536 in a recognized International Depositary Authority under the Budapest Treaty (1977), the International Mycological Institute (IMI), Bakeham Lane, Englefield Green, Egham, Surrey, TW20 9TY, UK.

Filiation

The new strain has been obtained from *Penicillium funiculosum* IMI 134756 after successive UV and β-irradiations treatment of spores, including screening on selective medium. No genetic modification has been obtained by recombinant DNA techniques using inclusion of foreign DNA or RNA.

Identification and Typing

*Penicillium funiculosum* IMI 378536 has been characterised by growth on Czapek Dox agar at 25° C. Colony characteristics and micro-morphology are typical for *Penicillium funiculosum*. The identification of the microorganism as a *Penicillium funiculosum* has been confirmed at the International Mycological Institute, Bakeham Lane, Englefield Green, Egham, Surrey, TW20 9TY, UK. Growth is as a tough basal felt, with aerial growth, as ropes or bundles of hyphae (funiculose), mycelium is white with underlying red colouration in the substrate, margins are reverse pale but coloured red towards centres and may become deep red. This penicillium is typical, it shows conidiophores short mostly arising from funicles, biverticillate, acerose conidiogenous cells, conidia are elliptical and smooth.

The micro-organism used for the production of the enzyme preparation of this invention is grown under aerobic conditions in a medium which contains cellulose, corn steep liquor, calcium carbonate and ammonium sulphate.

B. Process of Fermentation

This new fungus is manufactured by fermentation of the deposited strain first on a seed medium preferably constituted of (in weight):

| | |
|---|---|
| corn steep liquor | 1% to 4% |
| antifoam | just to avoid foam |
| water | to 100% |
| NaOH | enough to adjust the pH to about pH 3.0 to 6.0 before sterilisation of the medium; |
| Temperature of incubation | 27° C. to 36° C. |

The production medium has preferably the following constitution (in weight):

| | |
|---|---|
| corn steep liquor | 0 to 4.0% |
| batched and fed cellulose | 0.8 to 14% |
| Ca salt, | 0 to 0.8% |
| Ammonium sulfate | 0 to 1.0% |
| Antifoam | just to avoid foam |
| water | enough to obtain 100% |
| NaOH | enough to adjust the pH to about pH 3.0 to 6.0 before sterilisation of the medium; |
| $H_2SO_4$ | enough to maintain the pH to about 3.0 to 6.0; |
| Ammonia as gas or liquid | enough to maintain the pH to about pH 3.0 to 6.0; |
| Temperature of incubation | 27° C. to 36° C. |

For the fermentation, charge the fermenter with sufficient water, add the ingredients to water in suitable agitated container, stir until the ingredients have dissolved. Sterilise by sealing the fermentor and raising the content to typically 121° C. The fermentation vessel is inoculated with the seed fermenter.

The main source of carbon which is added during the process of fermentation is cellulose ; amongst different cellulose sources we prefer to use ARBOCEL, SOLKAFLOC, CLAROCEL, ALPHACEL, FIBRACEL with different grades.

The pH during the fermentation is preferably controlled by the addition of sulphuric acid, or another acid, and ammonia in gas or liquid form, or another base.

At the end of the fermentation time, eliminate solids by solid-liquid separation such as filtration or centrifugation, collect the liquid phase and concentrate for example by ultrafiltration on organic or mineral membrane.

These enzymes may also be manufactured from means of recombinant DNA technology and thus be produced by recombinant homologous species or heterologous species. The host for the transfer of the gene coding for the enzyme may be selected from a fungal species, a bacterial cell or a plant cell. Any conventional technique may be used to insert the gene encoding the enzyme of interest in the host cell such as plasmids (integrative or not), phage vectors and viral vectors. The *Penicillium funiculosum* comprising heterologous genes inclusion or modification of the genome with homologous genes by inclusion, deletion or modification of said homologous gene are also part of this invention.

In accordance with the invention the enzyme may be provided as an isolated pure enzyme preparation or as a crude preparation such as the cultivation medium in which *Penicillium funiculosum* has been grown.

It may be also possible to include this or those enzymes in compositions containing one further enzyme, the type of which depending on the intended use of the composition. The added enzymes may be selected from for example carbohydrases, lipases and proteases.

C. Compositions of the <<Mixture of Enzyme Activities>>

1. Liquid Composition

For liquid composition, after addition of antimicrobial agents measurement of the concentration of enzymes and correct dilution to product strength is carried out.

The preferred composition of the liquid solution by weight is the following:

| | |
|---|---|
| Microbial products as total organic solids | 4%–10% |
| antimicrobial agent | 0,005%–0,35% |
| preferentially | 0,01%–0.25% |
| sorbitol | 20%–50% |
| eventually antifreezing agents | 0–40% |
| more preferably | 15%–40% |
| Concentrated filtered fermentation broth | 0.3 to 76% |
| Buffered and adjusted to pH 3 to 5 | |

Antimicrobial are chosen from products such as sorbic acid and salts, benzoic acid and salts, methyl 4-hydroxybenzoate and n-propyl 4-hydroxybenzoate, fumaric acid, salts and esters. Salts such as sodium chloride or potassium chloride could also be used.

The most preferred anti-freezing agents are 1,2-propandiol, ethylene glycol, glycerol.

2. Powder Composition

For powder preparations, the concentrated solution obtained is dried with eventually the presence of a carrier. The powder obtained after drying of the concentrated solution in absence of a carrier can be further mixed with a suitable carrier.

The preferred composition of the powder form is the following:

| | |
|---|---|
| Microbial products as total organic solids | 16%–40% |
| Carrier | 59%–83% |
| other dried fermentation broth components | 1% |

Preferred carriers are chosen from wheat flour, starch, gypsum, maltodextrin, corn solids, by-products from cereal processing such as maize grits, wheat middlings, wheat bran, rye tailings, minerals mixture.

$$F_r = \frac{T_{substrate} - T_{water}}{T_{test} - T_{water}} \quad F_r = \frac{T_{substrate} - T_{water}}{T_{test} - T_{water}}$$

D. Enzyme characteristics

We obtain a new enzymes mixture produced by *Penicillium funiculosum*. This enzymes mixture contains new enzymes such as cellulases, β-glucanases, xylanases, xylanase accessory enzymes such as arabinofuranosidase and feruloyl esterases.

1. Procedure

The enzyme preparation is characterised by assays that include assays for cellulase, cellobiohydrolase, β-glucosidase, endo-1,3(4)-β-glucanase, laminarinase endo-1,4-β-xylanase (using different substrates), β-xylosidase, arabinofuranosidase and feruloyl esterase (using different substrates) activities.

1.1. Cellulase by DNS CMC Method

The assay for cellulase activity is based on the enzymatic hydrolysis of the glycosidic bonds in carboxymethylcellulose (CMC), a β-1,4 glucan. The products of the reaction, β-1,4 glucan oligosaccharides, are determined by the resulting increase in reducing value (as glucose).

A solution containing 1 ml of a 1%(w/v) CMC solution in 0.1M sodium acetate buffer, pH 5.0 (or at different pH values); 1 ml of appropriately diluted enzyme solution was incubated at 50° C. for 10 minutes. The enzyme reaction is stopped by the addition of 2 ml of a DNS solution (1%(w/v) 3,5-dinitrosalicylic acid, 1.6%(w/v) sodium hydroxide, 30% (w/v) potassium sodium (+)-tartrate in distilled water). The solution is mixed and placed into a boiling water bath, 95° C. minimum, for 5 minutes then cooled to 25° C. 10 ml distilled water is added to the solution and the absorbance is measured at 540 nm using a 2 cm path length glass cell.

The result is converted to μmoles reducing sugar (as glucose) by comparison with a standard curve for 2 ml of 0.00–0.04%(w/v) glucose solutions treated with DNS solution in an equivalent manner.

The observed enzyme reaction absorbance is corrected for non-specific absorbance by carrying out a reaction in which the DNS solution is added to the mixture before the enzyme solution. One unit of cellulase activity is defined as the amount of enzyme which produces 1 μmole glucose equivalents.$min^{-1}$ under the conditions of the assay (50° C. and pH 5.0 or other pH).

1.2 Cellobiohydrolase by the p-Nitrophenyl β-D-Cellobiopyranoside Method

The assay of cellobiohydrolase is based on the enzymatic hydrolysis of p-nitrophenyl β-D-cellobiopyranoside. A product of the reaction, p-nitrophenol is determined colorimetrically.

A solution containing 1 ml of a 0.1%(w/v) p-nitrophenyl β-D-cellobiopyranoside in distilled water: 1 ml distilled water; 1 ml 0.2M sodium acetate buffer, pH 5.0; 1 ml of appropriately diluted enzyme solution was incubated at 50° C. for 30 minutes. The enzyme reaction is stopped by the addition of 4 ml of 0.4M glycine solution. The solution is mixed and cooled to 20° C. The absorbance is measured at 400 nm using a 1 cm path length glass cell.

The result is converted to μmoles p-nitrophenol by comparison with the molar extenction coefficient of p-nitrophenol under these conditions.

The observed enzyme reaction absorbance is corrected for non-specific absorbance by carrying out a reaction in which the glycine solution is added to the mixture before the enzyme solution. One unit of cellobiohydrolase activity is defined as the amount of enzyme which produces 1 μmole p-nitrophenol from p-nitrophenyl β-D-cellobiopyranoside per minute under the conditions of the assay (50° C. and pH 5.0).

1.3 β-Glucosidase by the p-Nitrophenyl β-D-Glucopyranoside Method

The assay of β-glucosidase is based on the enzymatic hydrolysis of p-nitrophenyl β-D-glucopyranoside. A product of the reaction, p-nitrophenol is determined colorimetrically.

A solution containing 1 ml of a 0.1%(w/v) p-nitrophenyl β-D-glucopyranoside in distilled water; 1 ml distilled water; 1 ml 0.2M sodium acetate buffer, pH 5.0; 1 ml of appropriately diluted enzyme solution was incubated at 50° C. for 30 minutes. The enzyme reaction is stopped by the addition of 4 ml of 0.4M glycine solution. The solution is mixed and cooled to 20° C. The absorbance is measured at 400 nm using a 1 cm path length glass cell.

The result is converted to μmoles p-nitrophenol by comparison with the molar extenction coefficient of p-nitrophenol under these conditions.

The observed enzyme reaction absorbance is corrected for non-specific absorbance by carrying out a reaction in which the glycine solution is added to the mixture before the enzyme solution. One unit of β-glucosidase activity is defined as the amount of enzyme which produces 1 μmole p-nitrophenol from p-nitrophenyl β-D-glucopyranoside per minute under the conditions of the assay (50° C. and pH 5.0).

1.4. endo-1,3(4)-β-Glucanase by the DNS Barley β-Glucan Method

An assay for endo-1,3(4)-β-glucanase activity is based on the enzymatic hydrolysis of the glycosidic bonds in barley β-glucan, a β-1,3(4)-glucan. The products of the reaction, β-1,3(4)-glucan oligosaccharides, are determined by the resulting increase in reducing value (as glucose).

A solution containing 1 ml of a 1%(w/v) barley β-glucan solution in 0.1M sodium acetate buffer, pH 5.0 (or at different pH values); 1 ml of appropriately diluted enzyme solution was incubated at 50° C. for 10 minutes. The enzyme reaction is stopped by the addition of 2 ml of a DNS solution (1%(w/v) 3,5-dinitrosalicylic acid, 1.6%(w/v) sodium hydroxide, 30%(w/v) potassium sodium (+)-tartrate in distilled water). The solution is mixed and placed into a boiling water bath, 95° C. minimum, for 5 minutes then cooled to 25° C. 10 ml distilled water is added to the solution and the absorbance is measured at 540 nm using a 2 cm path length glass cell.

The result is converted to μmoles reducing sugar (as glucose) by comparison with a standard curve for 2 ml of 0.00–0.04%(w/v) glucose solutions treated with DNS solution in an equivalent manner.

The observed enzyme reaction absorbance is corrected for non-specific absorbance by carrying out a reaction in which the DNS solution is added to the mixture before the enzyme solution. One unit of endo-1,3(4)-β-glucanase activity is defined as the amount of enzyme which produces 1 μmole glucose equivalents.$min^{-1}$ under the conditions of the assay (50° C. and pH 5.0 or other pH).

1.5. endo-1,3(4)-β-glucanase by the azo Barley β-Glucan Method

An assay for endo-1,3(4)-β-glucanase activity is based on the enzymatic hydrolysis of a barley β-glucan which has a bound chromophore (azo-barley β-glucan). The products of the reaction, oligomers that are soluble after ethanol precipitation, are determined by the resulting increase in absorbance at 590 nm.

A solution containing 0.5 ml of azo barley β-glucan substrate (ready-to-use form) and 0.2 ml of enzyme dilution (containing between 0.15 to 0.60 units.$ml^{-1}$ in 0.01M sodium acetate buffer, pH 4.6) was incubated at 30° C. for 20 minutes exactly. The enzyme reaction is stopped by the addition of 2.5 ml of Precipitation Solution (containing 18.1 g sodium acetate and 3.0 g zinc mixed in 300 ml of glass distilled water, pH adjusted to pH 5.0 with hydrochloric acid, transfer contents to a 1 l volumetric flask and make up to volume with 96% v/v ethanol). The solution is mixed and allowed to stand at room temperature for 10 minutes. The solution is transfered in centrifuge tube and centrifuged at 1000 g for 10 minutes in a benchtop centrifuge. The absorbance of the supernatant is measured at 590 nm using a 1 cm path length glass cell.

The observed enzyme reaction absorbance is corrected for non-specific absorbance by carrying out a reaction in which the Precipitation Solution is added to the mixture before the enzyme solution. One unit of endo-1,3(4)-β-glucanase activity is defined as the amount of enzyme which hydrolyses the substrate to give an absorbance of 0.820 units at 590 nm, using a standard substrate, under the conditions of the assay (30° C. and pH 4.6).

1.6. Laminarinase (endo-1,3-β-Glucanase) by the DNS Laminarin Method

The assay for laminarinase (endo-1,3(4)-β-glucanase) activity is based on the enzymatic hydrolysis of the glycosidic bonds in laminarin, a β-1,3-glucan. The products of the reaction, β-1,3-glucan oligosaccharides, are determined by the resulting increase in reducing value (as glucose).

A solution containing 1 ml of a 1%(w/v) laminarin solution in 0.1M sodium acetate buffer, pH 5.0; 1 ml of appropriately diluted enzyme solution was incubated at 50° C. for 10 minutes. The enzyme reaction is stopped by the addition of 2 ml of a DNS solution (1%(w/v) 3,5-dinitrosalicylic acid, 1.6%(w/v) sodium hydroxide, 30%(w/v) potassium sodium (+)-tartrate in distilled water). The solution is mixed and placed into a boiling water bath. 95° C. minimum, for 5 minutes then cooled to 25° C. 10 ml distilled water is added to the solution and the absorbance is measured at 540 nm using a 2 cm path length glass cell.

The result is converted to μmoles reducing sugar (as glucose) by comparison with a standard curve for 2 ml of 0.00–0.04%(w/v) glucose solutions treated with DNS solution in an equivalent manner.

The observed enzyme reaction absorbance is corrected for non-specific absorbance by carrying out a reaction in which the DNS solution is added to the mixture before the enzyme solution. One unit of laminarinase activity is defined as the amount of enzyme which produces 1 μmole glucose equivalents.$min^{-1}$ under the conditions of the assay (50° C. and pH 5.0).

1.7. endo-1,4-β-Xylanase by the DNS Birchwood Xylan Method

An assay for endo-1,4-β-xylanase activity is based on the enzymatic hydrolysis of the xylosidic bonds in birchwood xylan, a β-1,4-xylan. The products of the reaction, β-1,4-xylan oligosaccharides are determined by the resulting increase in reducing value (as xylose).

A solution containing 1 ml of a 1%(w/v) birchwood xylan solution in 0.1M sodium acetate buffer, pH 5.0 (or at different pH values); 1 ml of appropriately diluted enzyme solution was incubated at 50° C. for 10 minutes. The enzyme reaction is stopped by the addition of 2 ml of a DNS solution (1%(w/v) 3,5-dinitrosalicylic acid, 1.6%(w/v) sodium hydroxide, 30%(w/v) potassium sodium (+)-tartrate in distilled water). The solution is mixed and placed into a boiling water bath, 95° C. minimum, for 5 minutes then cooled to 25° C. 10 ml distilled water is added to the solution and the absorbance is measured at 540 nm using a 2 cm path length glass cell.

The result is converted to μmoles reducing sugar (as xylose) by comparison with a standard curve for 2 ml of 0.00–0.03%(w/v) xylose solutions treated with DNS solution in an equivalent manner.

The observed enzyme reaction absorbance is corrected for non-specific absorbance by carrying out a reaction in which the DNS solution is added to the mixture before the enzyme solution. One unit of endo-1,4-β-xylanase activity is defined as the amount of enzyme which produces 1 μmole xylose equivalents.$min^{-1}$ under the conditions of the assay (50° C. and pH 5.0 or other pH).

1.8. endo-1,4-β-Xylanase by the DNS Wheat Arabinoxylan Method

An assay for endo-1,4-β-xylanase activity is based on the enzymatic hydrolysis of the xylosidic bonds in wheat arabinoxylan, an arabinose substituted β-1,4-xylan. The products of the reaction, arabino-β-1,4-xylan oligosaccharides are determined by the resulting increase in reducing value (as xylose).

A solution containing 1 ml of a 1%(w/v) wheat arabinoxylan solution in 0.1M sodium acetate buffer, pH 5.0 (or at different pH values); 1 ml of appropriately diluted enzyme solution was incubated at 50° C. for 10 minutes. The enzyme reaction is stopped by the addition of 2 ml of a DNS solution (1%(w/v) 3,5-dinitrosalicylic acid, 1.6%(w/v) sodium hydroxide, 30%(w/v) potassium sodium (+)-tartrate in distilled water). The solution is mixed and placed into a boiling water bath, 95° C. minimum, for 5 minutes then cooled to 25° C. 10 ml distilled water is added to the solution and the absorbance is measured at 540 nm using a 2 cm path length glass cell.

The result is converted to μmoles reducing sugar (as xylose) by comparison with a standard curve for 2 ml of 0.00–0.03%(w/v) xylose solutions treated with DNS solution in an equivalent manner.

The observed enzyme reaction absorbance is corrected for non-specific absorbance by carrying out a reaction in which the DNS solution is added to the mixture before the enzyme solution. One unit of endo-1,4-β-xylanase activity is defined as the amount of enzyme which produces 1 μmole xylose equivalents.$min^{-1}$ under the conditions of the assay (50° C. and pH 5.0 or other pH).

1.9. endo-1,4-β-Xylanase by the Viscometric Wheat Araboxylan Method

An assay for endo-1,4-β-xylanase activity is based on the enzymatic hydrolysis of a standard wheat arabinoxylan solution, the activity being determined by the reduction in relative viscosity against time.

A solution containing 1 ml of a 1%(w/v) wheat arabinoxylan solution in 0.1M sodium acetate buffer, pH 5.5 (or at different pH values); 3 ml distilled water and 1 ml of appropriately diluted enzyme solution is injected into a Haake microviscometer (using a gold ball calibrated to 0.1–2.0 mPa·s) and the ball drop time ($T_{test}$) measured (in ms over the defined drop length) every 30 seconds over a period of 15–20 minutes at 30° C. Mean ball drop times are measured for water (5 ml distilled water) and substrate (1 ml of a 1%(w/v) wheat arabinoxylan solution in 0.1M sodium acetate buffer, pH 5.5 and 4 ml distilled water) as $T_{water}$ and $T_{substrate}$ respectively. Controls are measured in an equivalent manner. The relative fluidity ($F_r$) is calculated for each value of $T_{test}$ as follows:

$$F_r = \frac{T_{substrate} - T_{water}}{T_{test} - T_{water}}$$

The slope of a plot of $F_r$ against time (the elapsed time at which each measurement of $T_{test}$ is made) is calculated in relative fluidity change per minute ($\Delta Fr.min^{-1}$) and is proportional to the enzyme concentration. One unit of endo-1,4-β-xylanase activity is defined as the amount of enzyme which will hydrolyse the substrate, reducing the viscosity of the solution, to give a change in relative fluidity of 1 (dimensionless unit).$min^{-1}$ under the conditions of the assay (30° C. and pH 5.5 or other pH).

1.10 β-Xylosidase by the p-Nitrophenyl β-D-Xylopyranoside Method

The assay of β-xylosidase is based on the enzymatic hydrolysis of p-nitrophenyl β-D-xylopyranoside. A product of the reaction, p-nitrophenol is determined colorimetrically.

A solution containing 1 ml of a 0.1%(w/v) p-nitrophenyl β-D-xylopyranoside in distilled water; 1 ml distilled water; 1 ml 0.2M sodium acetate buffer, pH 5.0; 1 ml of appropriately diluted enzyme solution was incubated at 50° C. for 30 minutes. The enzyme reaction is stopped by the addition of 4 ml of 0.4M glycine solution. The solution is mixed and cooled to 20° C. The absorbance is measured at 400 nm using a 1 cm path length glass cell.

The result is converted to μmoles p-nitrophenol by comparison with the molar extention coefficient of p-nitrophenol under these conditions.

The observed enzyme reaction absorbance is corrected for non-specific absorbance by carrying out a reaction in which the glycine solution is added to the mixture before the enzyme solution. One unit of xylosidase activity is defined as the amount of enzyme which produces 1 μmole p-nitrophenol from p-nitrophenyl β-D-xylopyranoside per minute under the conditions of the assay (50° C. and pH 5.0).

1.11 α-N-Arabinofuranosidase by the p-Nitrophenyl α-L-Arabinofuranoside Method

The assay of α-N-arabinofuranosidase (arabinofuranosidase) is based on the enzymatic hydrolysis of p-nitrophenyl α-L-arabinofuranoside. A product of the reaction, p-nitrophenol is determined colorimetrically.

A solution containing 1 ml of a 0.1%(w/v) p-nitrophenyl α-L-arabinofuranoside in distilled water; 1 ml distilled water; 1 ml 0.2M sodium acetate buffer, pH 5.0; 1 ml of appropriately diluted enzyme solution was incubated at 50° C. for 30 minutes. The enzyme reaction is stopped by the addition of 4 ml of 0.4M glycine solution. The solution is mixed and cooled to 20° C. The absorbance is measured at 400 nm using a 1 cm path length glass cell.

The result is converted to μmoles p-nitrophenol by comparison with the molar extention coefficient of p-nitrophenol under these conditions.

The observed enzyme reaction absorbance is corrected for non-specific absorbance by carrying out a reaction in which the glycine solution is added to the mixture before the enzyme solution. One unit of arabinofuranosidase activity is defined as the amount of enzyme which produces 1 μmole p-nitrophenol from p-nitrophenyl α-L-arabinofuranoside per minute under the conditions of the assay (50° C. and pH 5.0).

1.12 Feruloyl Esterase by the FAXX Method

An assay of feruloyl esterase (ferulic acid esterase) is based on the enzymatic hydrolysis of O-[5-O-(trans-feruloyl)-α-L-arabinofuranosyl]-(1→3)-O-β-D-xylopyranosyl-(1→4)-D-xyfopyranose (FAXX). FAXX is prepared from enzyme-hydrolysed wheat bran, purified and characterised by NMR. FAXX hydrolysis is measured spectophotometrically.

The enzyme reaction is followed at 325 nm, using a 1 cm path length cell, in solution containing 0.050 mM FAXX in 0.1M MOPS buffer, pH 6.0 at 37° C.

One unit of feruloyl esterase activity on FAXX is defined as the amount of enzyme which converts 1 μmole substrate to product per minute under the conditions of the assay (37° C. and pH 6.0).

1.13 Feruloyl Esterase by the $Ara_2F$ Method

An assay of feruloyl esterase (ferulic acid esterase) is based on the enzymatic hydrolysis of $Ara_2F$ (ferulic acid linked 1,2 to arabinose). $Ara_2F$ is prepared from enzyme-hydrolysed sugar beet pulp, purified and characterised by NMR. $Ara_2F$ hydrolysis is measured spectophotometrically.

The enzyme reaction is followed at 325 nm, using a 1 cm path length cell, in solution containing 0.050 mM $Ara_2F$ in 0.1M MOPS buffer, pH 6.0 at 37° C.

One unit of feruloyl esterase activity on $Ara_2F$ is defined as the amount of enzyme which converts 1 μmole substrate to product per minute under the conditions of the assay (37° C. and pH 6.0).

1.14 Feruloyl Esterase by the Hydrolysis of Methyl Esters: Methyl Ferulic Acid (MFA); Methyl Caffeic Acid (MCA); Methyl Sinapic Acid (MSA); Methyl p-Coumaric Acid (MPCA) Methods An assay of feruloyl esterase (ferulic acid esterase) is based on the enzymatic hydrolysis of methyl esters of ferulic acid (MFA), caffeic acid (MCA), sinapic acid (MSA) and p-coumaric acid (MpCA). Methyl ester hydrolysis is measured in 0.1M MOPS buffer, pH 6.0 at 37° C. Assays are based on two different techniques.

In the spectrophotometric method the methyl ester substrate concentration is 0.10 mM and ester hydrolysis is followed at 325 nm using a 1 cm path length cell. In this method the initial substrate concentration is limited.

In the HPLC method, the methyl ester substrate concentration is 1.0 mM and ester hydrolysis is followed at by measuring the release of free acid by HPLC after 10–30 minute intervals. In this method there is no limit over substrate concentration and activities measured are considerably higher than those for the spectrophotometric method.

One unit of feruloyl esterase activity is defined as the amount of enzyme which converts 1 μmole substrate to product per minute under the conditions of the assay (37° C. and pH 6.0).

1.15 Protein Concentration by Modified Bradford Coomassie Blue-binding Protein Assay The assay of protein concentration is based on the modified Bradford Coomassie blue-binding protein assay using Brilliant Blue G (Coomassie blue) measured in a spectrophotometer at 595 nm using 1 cm light path glass cuvettes. The method (Sigma B 6916) is standardised using Bovine Serum Albumin (Sigma P 0914).

1.16 Isoelectric Point by Isoelectric Focusing

Isoelectric points of proteins are determined by standard methods using pre-cast vertical 5% polyacrylamide gels such as gels from NOVEX® for pH 3–10 (pl performance range 3.5–8.5) or pH 3–7 (pl performance range 3.0–6.5) in the NOVEX® XCell II™ Mini-Cell. NOVEX® cathode, anode and IEF sample buffers for pH 3–10 or pH 3–7 are used. NOVEX® standard protocol for isoelectric focusing, fixing, staining with Coomassie R-250 Blue Stain, and destaining are used.

1.17 SDS-PAGE (Sodium Dodecylsulphate Polyacrylamide Gel Elctrophoresis)

Analytical separation and molecular weight determination of proteins are carried out standard SDS-PAGE methods. Pre-cast NOVEX® NuPAGE™ gels (NuPAGE™ Bis-Tris gels or NuPAGE™ Tris-Acetate gels with NOVEX® recommended running buffers) are used in the NOVEX® XCell II™ Mini-Cell. NOVEX® sample preparation and running buffers, and molecular weight standards are used. NOVEX® standard protocol for SDS-PAGE, fixing, staining with Coomassie R-250 Blue Stain, and destaining are used.

2. Results on the Enzymes Mixture 2.1. Optimal pH 2.1.1. Activity endo-1,3(4)-β-Glucanase The assay of endo-1,3(4)-β-glucanase from *Penicillium funiculosum* was carried out under standard conditions at 50° C. using the DNS barley β-glucan method. Enzyme activity was measured between pH 3.0 and pH 7.0. The optimal pH for enzyme activity is pH 4.0–5.0.

| | Activity | |
|---|---|---|
| pH | ($IU.ml^{-1}$) | (%) |
| 3 | 325 | 42 |
| 4 | 761 | 98 |
| 5 | 775 | 100 |
| 6 | 507 | 66 |
| 7 | 152 | 20 |

2.1.2. Activity endo-1,4-β-Xylanase

The assay of endo-1,4-β-xylanase from *Penicillium funiculosum* was carried out under standard conditions at 50° C. using the DNS birchwood xylan method.

| | Activity | |
|---|---|---|
| pH | ($IU.ml^{-1}$) | (%) |
| 2.0 | 3559 | 37 |
| 2.6 | 6700 | 70 |
| 3.0 | 8411 | 88 |
| 3.0 | 8113 | 85 |
| 3.5 | 9582 | 100 |
| 4.0 | 8523 | 89 |
| 4.0 | 8510 | 89 |
| 5.0 | 5544 | 58 |
| 5.5 | 3522 | 37 |
| 6.0 | 2190 | 23 |
| 7.0 | 1103 | 12 |

2.2. Optimal Temperature 2.2.1. Activity endo-1,3(4)-β-Glucanase

The assay of endo-1,3(4)-β-glucanase from *Penicillium funiculosum* was carried out under standard conditions at pH 5.0 (the optimal pH for this enzyme) using the DNS barley β-glucan method. Enzyme activity was measured between 30 and 70° C. The optimal temperature lies between 50 and 60° C. with the greatest activity being measured at 60° C. The results in detail, in the form of a table vs. temperature are given.

| | Activity | |
|---|---|---|
| Temperature | ($IU.ml^{-1}$) | (%) |
| 30 | 247 | 32 |
| 40 | 541 | 70 |
| 50 | 775 | 100 |
| 60 | 1082 | 140 |
| 70 | 774 | 98 |

2.2.2. Activity endo-1,4-β-Xylanase

The assay of endo-1,4-β-xylanase from *Penicillium funiculosum* was carried out under standard conditions at pH 5.5 and pH 3.5 using the DNS birchwood xylan method. Enzyme activity was measured between 30 and 70° C. The optimal temperature lies between 50 and 60° C. with the greatest activity being measured at 50° C. for pH 5.5 and at 60° C. for pH 3.5. The results in detail, in the form of a table vs. temperature are given.

| Temperature | Activity (pH 5.5) | | Activity (pH 3.5) | |
|---|---|---|---|---|
| (° C.) | ($IU.ml^{-1}$) | (%) | ($IU.ml^{-1}$) | (%) |
| 30 | 2492 | 41 | 4334 | 23 |
| 40 | 4042 | 66 | 8128 | 42 |
| 50 | 6107 | 100 | 18251 | 95 |
| 60 | 4602 | 75 | 19155 | 100 |
| 70 | 3851 | 63 | 12730 | 66 |

Enzymes produced by *Penicillium funiculosum* have high levels of cellulase, endo-1,3(4)-β-glucanase and other glycanolytic activities. In addition, they are also characterised by high levels of endo-1,4-β-xylanase and xylanase accessory enzyme activities. The broad spectrum of hemicellulolytic enzymes is a characteristic of enzyme preparations from this micro-organism.

Each activity measured can reported as a ratio to a major activity for that preparation. An example of obtained results is shown in table A. These ratios may change in preparations from different fermentation batches.

TABLE A

Relative activities against relevant different substrates

| Methods used in the tests | Results with *Penicillium funiculosum* |
|---|---|
| Cellulase (DNS CMC method, pH 5.0) [1.1] | 3.14 |
| Cellobiohydrolase (p-nitrophenyl β-D-cellobiopyranoside method, pH 5.0) [1.2] | 0.022 |
| β-Glucosidase (p-nitrophenyl β-D-glucobiopyranoside method, pH 5.0) [1.3] | 0.157 |
| Endo-1,3(4)-β-glucanase (DNS barley β-glucan method, pH 5.0) [1.4] | 7.23 |
| Endo-1,3(4)-β-glucanase (azo-barley β-glucan method, pH 4.6) [1.5] | 1+/− |
| Laminarinase (DNS laminarin method, pH 5.0) [1.6] | 0.30 |
| Endo-1,4-β-xylanase (DNS birchwood xylan method, pH 3.5) [1.7] | 9.16 |
| Endo-1,4-β-xylanase (DNS wheat arabinoxylan method, pH 3.5) [1.8] | 8.67 |
| Endo 1,4-β xylanase (viscometric wheat arabinoxylan method, pH 5.5) [1.9] | 9.80 |
| β-Xylosidase (p-nitrophenyl β-D-xylobiopyranoside method) [1.10] | 0.0047 |
| α-N-Arabinofuranosidase (p-nitrophenyl α-L-arabinofuranoside method) [1.11] | 0.0017 |
| Feruloyl esterase (FAXX method) [1.12] | 0.000254 |
| Feruloyl esterase ($Ara_2F$ method) [1.13] | 0.000349 |
| Feruloyl esterase (MFA spectrophotometric method) [1.14] | 0.000135 |
| Feruloyl esterase (MCA spectrophotometric method) [1.14] | 0.000174 |
| Feruloyl esterase (MSA spectrophotometric method) [1.14] | 0.000049 |
| Feruloyl esterase (MpCA spectrophotometric method) [1.14] | 0.000216 |

3—Properties of Components in the Enzyme Mixture 3.1. Purification Methods

Hydrophobic Interaction Chromatography

The preparation obtained after filtration and concentration of the fermentation medium, to 112.6 mg/ml protein concentration, was diluted 1/1 with Hydrophobic Interaction Chromatogaphy (HIC) buffer (50 mM phosphate buffer, pH 7.0/1.7 M $(NH_4)_2SO_4$/0.04% sodium azide), exchanged into HIC buffer (PD-10 columns; Phamacia). Portions (10 ml) were applied to a column (10×5 cm diameter, 200 ml) of PhenylSepharose™ high performance HIC gel (Pharmacia) and separated using a gradient of reducing ammonium sulphate $(NH_4)_2SO_4$)concentration (1.7–0.0 M) at 10 ml/min. Fractions (10 ml) were collected and assayed for xylanase activity.

HIC gave two major peaks of xylanase activity. The first, named A, eluted from the column when the $NH_4)_2SO_4$ concentration was reduced to about 0.6 M, while the second, named B, eluted at about 0.25 M $NH_4)_2SO_4$ concentration. Fractions comprising peaks A and B from each injection were pooled separately. In total fraction A corresponded to 2.8% of the total xylanase activity whilst fraction B corresponded to 97.2% of the total xylanase activity. The yield was 77%.

Ion-Exchange Chromatography

Pooled fractions for peak A and B from HIC were precipitated by increasing the $NH_4)_2SO_4$ concentration to 100% saturation followed by centrifugation (10 000×g for 30 minutes). Pellets were redissolved in 20 mM Tris-HCl buffer, pH 8.0/0.04% sodium azide and desalted to the same buffer using PD-10 columns. Samples (5 ml) were applied to a MonoQ™ HR 10/10 anion-exchange column (Pharmacia) previously equilibrated with 20 mM Tris-HCl buffer, pH 8.0/0.04% sodium azide and eluted at 2 ml/min with increasing concentration of sodium chloride (NaCl (0–1 M) in the same buffer. Fractions (2 ml) were collected and assayed for xylanase activity.

Peak A:

Separation of peak A by anion-exchange chromatography gave a single peak of xylanase activity which eluted at about 0.3M NaCl. The most active fractions were pooled and analysed by SDS-PAGE (sodium dodecylsulphate polyacrylamide gel electrophoresis). This showed a single major band of molecular weight 48 kDa. Recovery of xylanase activity after IEF (isoelectric focusing) confirmed that this major Coomassie-stained band was a xylanase.

Peak B:

Separation of peak B by anion-exchange chromatography gave two major peaks of xylanase activity, one of which eluted in the void (unbound material; peak B-I) and the other at 0.1 M NaCl (peak B-II). There were also two minor peaks eluting at 0.13 M and 0.19 M NaCl. The active fractions corresponding to each peak were pooled and analysed by SDS-PAGE, but none of the samples were pure.

Gel Filtration Chromatography

Pooled fractions comprising B-I and B-II were freeze dried, redissolved in water, and desalted (using PD-10 columns). Samples (0.2 ml) were applied to a Superdex™ 75 HR column (Pharmacia) and eluted at 0.4 ml/minute with 20 mM Bis-Tris buffer, pH 6.0/0.2 M NaCl/0.04% sodium azide. Fractions (0.4 ml) were collected and assayed for xylanase activity.

3.2. Properties of Xylanases 3.2.1 Isoelectric Point by Isoelectric Focusing

Isoelectric points of proteins are determined by standard methods using pre-cast vertical 5% polyacrylamide gets from NOVEX® for pH 3–10 and pH 3–7. NOVEX® cathode, anode and IEF sample buffers, and standard protocol for isoelectric focusing, fixing, staining with Coomassie R-250 Blue Stain, and destaining are used.

For xylanase A, a sample following MonoQ was used. For xylanases B-I and B-II, a sample following HIC, xylanase B, was used. For each of A and B, a small sample (10 μl) was loaded into a single well and a large sample (50 μl) was loaded into a triple well. After focussing the samples, the gel was cut in half such that one half contained the two small samples (A+B) and the molecular weight markers (this half was stained with Coomassie), while the other half contained the two large samples. The gel half containing the large samples was cut to separate the two samples lanes, and subsequently each lane was fractionated into 2 mm pieces. Each 2 mm piece was soaked separately overnight in 100 mM MOPS buffer, pH 6.0/0.04% sodium azide. Fractions were assayed for xylanase activity.

For xylanase sample A, the stained IEF gel showed a single major band of pl 3.55 marker and a few minor contaminating bands. Xylanase activity was found only in the fraction corresponding to this band, confirming the xylanase major band.

For xylanase sample B, the stained IEF gel indicates several bands over a range of pl values. Xylanase activity occured in two separated fractions of the unstained gel, and corresponding to proteins of pl 4.2 and 4.8.

3.2.2 Molecular Weight by SDS-PAGE

To confirm the molecular weights of xylanases in peak B from HIC, the fractions with xylanase activity eluted from the IEF gel were deslated, freeze-dried, and separated by SDS-PAGE. Denaturing PAGE was performed using 10% Tris-glycine gels (NOVEX®) with dithiothreitol (DTT 50 mM) included in the sample buffer as a reducing agent.

The stained gel indicated that both xylanases were pure, with molecular weights of 36 kDa and 15 kDa for xylanase B-I and xylanase B-II respectively.

All three purified xylanases were subjected to SDS-PGE analysis, xylanase A fraction after anion-exchange chromatography, xyalanase B-I and B-II fractions after gel filtration chromatography. Xylanase A gave a single band of molecular weight 48 kDa. Xylanase B-I gave one major and four minor bands after Coomassie staining. The major band was confirmed as the xylanase since it was of molecular weight 36 kDa. The purity is estimated at 90%. Xylanase B-II gave a major band of molecular weight 15 kDa and 2–3 minor bands. This xylanase is approximately 95% pure.

| Sample | M.W. (kDa) | P.I. |
|---|---|---|
| Xylanase A | 48 | 3.55 |
| Xylanase B-I | 36 | 4.20 |
| Xylanase B-II | 15 | 4.80 |

3.2.3 Enzyme Activity

The tests for enzyme activity measurement are described previously.

3.2.3.1 Analysis of Xylanase A

| [Protein] 0.4 (mg/ml) | | | |
|---|---|---|---|
| | | Enzyme activity | |
| Enzyme assay method | pH | (u/ml) | (u/mg protein) |
| Cellulase (DNS CMC method) [1.1] | 5.0 | <1.0 | n/a |
| Cellobiohydrolase (p-nitrophenyl β-D-cellobiopyranoside method) [1.2] | 5.0 | <0.1 | n/a |
| Endo-1,3(4)-β-glucanase (DNS barley β-glucan method) [1.4] | 5.0 | <1.0 | n/a |
| Laminarinase (DNS laminarin method) [1.6] | 5.0 | nd | n/a |

-continued

| [Protein] 0.4 (mg/ml) | | | |
|---|---|---|---|
| | | Enzyme activity | |
| Enzyme assay method | pH | (u/ml) | (u/mg protein) |
| Endo-1,4-β-xylanase (DNS birchwood xylan method) [1.7] | 5.5 | 140 | 350 |
| Endo-1,4-β-xylanase (DNS birchwood xylan method) [1.7] | 3.5 | 158 | 395 |
| Endo-1,4-β-xylanase (DNS wheat arabinoxylan method) [1.8] | 5.5 | 152 | 380 |
| Endo-1,4-β-xylanase (DNS wheat arabinoxylan method) [1.8] | 3.5 | 171 | 429 |
| Endo 1,4-β xylanase (viscometric wheat arabinoxylan method) [1.9] | 5.5 | 456 | 1140 |

nd not determined
n/a not applicable

Xylanase Activity on Birchwood Xylan vs pH

| | ENZYME ACTIVITY | |
|---|---|---|
| pH | (IU/mg protein) | (% of maximum activity) |
| 2.00 | 294 | 73 |
| 3.00 | 353 | 87 |
| 3.50 | 385 | 95 |
| 4.00 | 405 | 100 |
| 5.00 | 345 | 85 |
| 5.50 | 340 | 84 |
| 6.00 | 302 | 75 |
| 7.00 | 212 | 52 |

3.2.3.2 Analysis of Xylanase B-I

| [Protein] 0.096 (mg/ml) | | | |
|---|---|---|---|
| | | Enzyme activity | |
| Enzyme assay method | pH | (u/ml) | (u/mg protein) |
| Cellulase (DNS CMC method) [1.1] | 5.0 | 26.5 | 276 |
| Cellobiohydrolase (p-nitrophenyl β-D-cellobiopyranoside method) [1.2] | 5.0 | 0.541 | 5.6 |
| Endo-1,3(4)-β-glucanase (DNS barley β-glucan method) [1.4] | 5.0 | 73.8 | 769 |
| Laminarinase (DNS laminarin method) [1.6] | 5.0 | <0.1 | n/a |
| Endo-1,4-β-xylanase (DNS birchwood xylan method) [1.7] | 5.5 | 51.3 | 534 |
| Endo-1,4-β-xylanase (DNS birchwood xylan method) [1.7] | 3.5 | 83.6 | 871 |
| Endo-1,4-β-xylanase (DNS wheat arabinoxylan method) [1.8] | 5.5 | 93.2 | 971 |
| Endo-1,4-β-xylanase (DNS wheat arabinoxylan method) [1.8] | 3.5 | 143.8 | 1498 |
| Endo 1,4-β xylanase (viscometric wheat arabinoxylan method) [1.9] | 5.5 | 147 | 1531 |

nd not determined
n/a not applicable

Xylanase Activity on Birchwood Xylan vs pH

| | ENZYME ACTIVITY | |
|---|---|---|
| pH | (IU/mg protein) | (% of maximum activity) |
| 2.00 | 610 | 70 |
| 3.00 | 755 | 87 |
| 3.50 | 871 | 100 |
| 4.00 | 802 | 92 |
| 5.00 | 567 | 65 |
| 5.50 | 534 | 61 |
| 6.00 | 481 | 55 |
| 7.00 | 404 | 46 |

3.2.3.3 Analysis of Xylanase BII

| [Protein] 0.165 (mg/ml) | | | |
|---|---|---|---|
| | | Enzyme activity | |
| Enzyme assay method | pH | (u/ml) | (u/mg protein) |
| Cellulase (DNS CMC method) [1.1] | 5.0 | <1.0 | n/a |
| Cellobiohydrolase (p-nitrophenyl β-D-cellobiopyranoside method) [1.2] | 5.0 | <0.1 | n/a |
| Endo-1,3(4)-β-glucanase (DNS barley β-glucan method) [1.4] | 5.0 | <1.0 | n/a |
| Laminarinase (DNS laminarin method) [1.6] | 5.0 | nd | n/a |
| Endo-1,4-β-xylanase (DNS birchwood xylan method) [1.7] | 5.5 | 141.9 | 860 |
| Endo-1,4-β-xylanase (DNS birchwood xylan method) [1.7] | 3.5 | 261.0 | 1582 |
| Endo-1,4-β-xylanase (DNS wheat arabinoxylan method) [1.8] | 5.5 | 152.6 | 925 |
| Endo-1,4-β-xylanase (DNS wheat arabinoxylan method) [1.8] | 3.5 | 267.9 | 1624 |
| Endo 1,4-β xylanase (viscometric wheat arabinoxylan method) [1.9] | 5.5 | 262 | 1588 |

nd not determined
n/a not applicable

Xylanase Activity on Birchwood Xylan vs pH

| | ENZYME ACTIVITY | |
|---|---|---|
| pH | (IU/mg protein) | (% of maximum activity) |
| 2.00 | 1374 | 84 |
| 3.00 | 1523 | 93 |
| 3.50 | 1582 | 97 |
| 4.00 | 1630 | 100 |
| 5.00 | 1093 | 67 |
| 5.50 | 860 | 53 |
| 6.00 | 443 | 27 |
| 7.00 | 156 | 10 |

3.2.4 Sequences

One embodiment of the present invention is related to the amino acid and the nucleic acid sequences of the above described proteins or their variants.

For this purpose, the sequences for xylanases were identified from amino acid sequences of purified proteins (xylanase A, xylanase B-I and xylanase B-II) and from comparisons of amino acid and nucleotide sequences of known fungal xylanases.

It is understood for the invention that variants refers to any polypeptide or any protein analog, protein fragment, derived or mutated protein from the native protein or polypeptide and having the same biological fuctions as the said native protein or polypeptide. Different variants may be exist at natural state. Those variants may be for example allelic variations characterized by differencies into the sequence of genes encoding for the said protein or may result from differential splicing or from post-traductional modifications. Variants are obtainable by substitution, deletion, addition and/or modification of one or more amino acids. The all modifications are well known and can be performed by any method known of one skilled in the art.

Variants are molecules having for example more affinity for their substrate or having new biological properties.

Another object of the present invention is also the use of the sequences for the expression of the disclosed proteins or polypeptides in host cells of uni- or pluricellular organisms. For this purpose, the said sequences may be comprised into the genome of a vector. The said vector may be a plasmid, a phage or a virus. In hence, another embodiment of the invention is a host isolated cell from uni- or pluricellular organism, transfected or infected by a vector as above described. In a preferred embodiment the host cell is a bacteria.

The use of said vectors comprising the nucleic acid sequence of the disclosed proteins for the expression of said protein in any host cell is another embodiment of the present invention.

3.2.4.1 Sequences of Xylanase C

The production of probes was based on comparisons of amino acid and nucleotide sequences of known fungal xylanases. Conserved regions were identified and used to design PCR primers, whose products would be used to screen a genomic library of *Penicillium funiculosum.*

Two pairs of degenerate primers were made. The first pair were designed to amplify a 200 pb (approximate) product from a xylanase type B (or type 2) gene. The second pair were designed to amplify a 250 bp product from a xylanase type A (or type 1) gene.

A 258 bp band was produced with primers 3 and 4. After cloning into pGEMT and sequencing this was found to have significant sequence similarity to fungal xylanase type A/1. The plasmid containing the cloned product has been named pPFXYLA.

The complete sequence of xylanase C is shown in FIG. 1 and in SEQ ID NO 1.

3.2.4.2 sequences of Xylanase BI

The internal amino acid sequence, together with sequence alignments of other fungal cellobiohydrolases were used to design degenerate PCR primers (SEQ ID NO 3 and NO 4). A 290 bp product (SEQ ID NO 5) was amplified and cloned into pGEMT(Promega) to create pGEMTCB2 and sequenced. As shown in FIG. 2, the primer sequences are underlined. This PCR product is currently being used as a probe to screen a *Penicillium funiculosum* IMI134756 genomic library.

3.2.4.3 Sequences of Xylanase BII

The all sequence of the xylanase BII gene includes 1.3 kb of 5' untranslated and upstream region and 0.85 kb of 3' untranslated, a 54 bp intron and 669 bp encoding a 223 amino acid protein Reverse transcription-PCR (RT-PCR) was used to prove the existence of the 54 bp intron. Total RNA was isolated from mycelia of *Penicillium funiculosum* IMI-134756 cultures, harvested after 4 days growth on 1% (w/v) oat spelt xylan. Primers were designed to amplify up to 195 bp fragment from messenger RNA (249 bp from genomic DNA) and to 433 bp (487 bp with genomic DNA).

Sequencing of 3 kb at the 3' end of the plasmid (pPFXYNC2, revealed a gene (designated per A) that contains two putative introns and encodes a polypeptide of aproximatively 570 amino acids. The polypeptide showed significant sequence similarity to fungal amino acid permeases.

3.2.4.4 Sequence of Xylanase A

The internal sequence of Xylanase A was obtained and is represented by the following amino acid sequence:

AEAINYNQDY (SEQ ID NO 10)

3.3 Properties of Feruloyl Esterases 3.3.1 Purification

It is carried out following the same process as for xylanases.

The enzymes mixture contains at least two distinct feruloyl esterases. One of these (FaeB) has a molecular weight of 38,945–41,051 Da by mass spectrometry (35.450 Da from the primary amino acid sequence and 37 kDa by SDS-PAGE). FaeB has a pl of 4.2, it is a type B feruloyl esterase and is specific for MpCA and $Ara_2F$ substrates (activity against MpCA, MCA, MFA and $Ara_2F$; but not against MSA and FAXX).

The other feruloyl esterase (FaeA) has a molecular weight of 29 kDa (by SDS-PAGE). FaeA has a pl of 4.65, it is a type A feruloyl esterase and is specific for FAXX and MSA substrates (activity against MSA, MCA, MFA and FAXX but not MpCA $Ara_2F$).

3.3.2. Isoelectric Point by Isoelectric Focusing

Isoelectric points of proteins are determined by the standard methods. The enzymes mixture was applied as a wide strip (about 20 mm) to an IEF gel and electrophoresed at reduced temperature (5° C.). After focusing and band sharpening, the gel was cut down the middle of the sample lane. One half of the sample lane and the IEF standards were fixed, stained and destained using the standard protocol. The other half lane was cut into 2 mm wide sections and each section soaked overnight in 1 ml of 100 mM MOPS buffer, pH 6.0. Feruloly esterase activity was determined for each section of the gel using MFA, MPCA and MSA as substrates.

The stained IEF gel indicates the presence of very many proteins in cellulase with pl's ranging from very acidic (pl 2.4) to about pl 7. Most of the proteins are acidic (pl range 2.4–5). Two peaks of feruloyl esterase activity were detected in fractions cut from the gel. One, corresponding to FaeB, had a pl of 4.2 and activity only against MFA and MpCA (not MSA). The other, corresponding to FaeA, had a pl of 4.65 and activity against all three substrates tested .

3.3.3 Molecular Weight by SDS-PAGE

Molecular weights were analysed by SDS-PAGE using 10% Tris-Glycine gels. SDS-PAGE gels were run, fixed, stained with Coomassie Blue Stain and destained using the standard protocol.

The enzymes mixture contains at least two distinct feruloyl esterases. One corresponding to FaeB (pl 4.2) has a molecular weight of 37 kDa. The other, corresponding to FaeA (pl 4.65) has a molecular weight of 29 kDa.

The molecular weight of FaeB is estimated at 34,450 Da from the primary amino acid sequence, and at 38,945–41,051 Da by mass spectrometry.

3.3.4 Feruloyl Estease Activity

Assays for feruloyl esterase activity performed on the enzymes mixture using the spectrophotometric method

| | Activity | |
|---|---|---|
| Substrate | (U/ml) | (U/g protein) |
| Methyl ferulate MFA (0.1 mM) | 0.086 | 7.9 |
| Methyl caffeate MCA (0.1 mM) | 0.111 | 10.3 |
| Methyl sinapate MSA (0.1 mM) | 0.031 | 2.9 |
| Methyl p-coumarate MpCA (0.1 mM) | 0.138 | 12.7 |
| FAXX (0.05 mM) | 0.162 | 15.0 |
| $Ara_2F$ (0.05 mM) | 0.222 | 20.6 |

The enzymes mixture contains activity against all the substrates tested. With the methyl esters, activity is highest against MpCA and lowest against MSA. The activities against $Ara_2F$ and FAXX are higher than against the methyl esters which is indicative that the esterase activities are due to true feruloyl esterases and not general esterases or side activities of other cell wall-degrading esterases (e.g. acetyl xylan esterase, pectin esterase).

3.3.5 Sequences 3.3.5.1 Sequence of FEA-A

According to trypsin digests of the purified protein internal amino acid sequences were obtained as shown as following:

Sequence 1 (SEQ ID NO 11)

QYTLTLPSNYNPNK

Sequence 2 (SEQ ID NO 12)

AVAVMSGANL

Sequence 3 (SEQ ID NO 13)

TEYSG(C/A)DSEHPVWWIAFDGP

Sequence 4 (SEQ ID NO 14)

DTFVKDDHCTPTNPPAPAAGSGTHIKYV

Several degenate PCR primers were designed from amino acid sequences obtained from the purified protein. Many products were cloned into pGEMT(Promega) and sequenced.

A plasmid named pGEMTD19 (180 bp) (FIG. 3) was found by PCR to contain sequence that was recognisable as peptide sequence 4 shown above. As shown in FIG. 3, the primer sequences have been double underlined previously known sequence, singly underlined.

The nucleic acid and amino acid sequences of FAE-A are disclosed in SEQ ID NO 7.

3.3.5.2 Sequence of FEA-B

Primers designed from peptide sequence of FAE-B were used to amplify up a probe, that was subsequently used to screen a *Penicillium funiculosum* genomic library. A 2291 bp clone was isolated and has been sequenced (SEQ ID ). The gene encoding for a 304 amino acid polypeptide and has one putative intron. The predicted amino acid sequence is shown in FIG. 4 SEQ ID NO. 9 wherein the mature protein (mature protein length=338) is in Bold. This protein comprises two distinct domains separated by a highly glycosylated linker. As shown in FIG. 4, the catalytic domain is in Bold, whereas the binding domain is in Bold double underlined and the linker is represented in dotted Bold line.

The protein is also featured by a putative active site motif (serine=nucleophile) as shown underlined in FIG. 4 with the following Putative catalytic triads:

(1) S1361/D174/H216

(2) S136/D2201/H276.

The FAE-B protein comprises also a secretion sequence (353) and 10 cysteines.

3.4 Properties of Glucanases

The enzymes mixture was subjected to 2D gel electrophoresis. IEF was carried out using pre-cast vertical 5% polyacrylamide gels from NOVEX® for pH 3–7 (pl performance range 3.0–6.5) in the NOVEX® XCell II™ Mini-Cell. NOVEX® cathode, anode and IEF sample buffers for pH 3–7 and the NOVEX® standard protocol for isoelectric focusing are used. One lane was cut off and electrophoresed in the second dimension using a 10% Laemmli SDS-PAGE gel. A second lane was separated from the gel, cut into 35 fractions, the gel strips soaked in buffer, and fractions assayed for enzyme activity. The third lane was left on the gel, fixed, stained with Coomassie R-250 Blue Stain and destained using the NOVEX® standard protocol.

Significant endo-1,3(4)-β-glucanase (DNS barley β-glucan method) and cellulase (DNS CMC method) activities were found in fractions corresponding to proteins with pl 4.2, M.W. 36 kDa and pl 5.4, M.W. 27 kDa. To eliminate Xylanase B-I as being in one of the fractions, the fractions were tested for activity using the DNS birchwood xylan method. No xylanase activity was detected in the fractions corresponding to β-glucanase or cellulase activities.

BRIEF DESCRIPTION OF THE DRAWINGS

FIG. 1: *Penicillium funiculosum* xylanase C protein amino acid sequence (SEQ ID NO:2).

FIG. 2: Nucleotide and amino acid sequences of xylanase BI (XynBI) PCR product (SEQ ID NO:6).

FIG. 3: Nucleotide and amino acid sequences of Feruloyl estease A (faeA) PCR product ((SEQ ID NO:9).

FIG. 4: *Penicillium funiculosum* Feruloyl estease B (faeB) protein (FAE-V or FAE-I) amino acid sequence (SEQ ID NO:9).

E. USES OF ENZYMES MIXTURE TO FEED ANIMALS

EXAMPLE 1

Evaluation of Enzymes Preparation Produced by *Penicillium funiculosum* Efficacy on Energy value ($AME_N$) of Mixed Wheat-barley Diet in Broilers The aim is to demonstrate the efficacy of enzymes (activity of β-glucanase: 100 $U.kg^{-1}$ and activity of xylanase: 1100 U. $kg^{-1}$) on Apparent Metabolizable Energy corrected for nitrogen balance ($AME_N$) of a diet containing 50% wheat and 22% barley. Experiences are led on Control and Enzymes Preparation (activity of β-glucanase: 100 $U.kg^{-1}$ and activity of xylanase: 1100 U. $kg^{-1}$) using the European Reference Method (Bourdillon et al., 1990) with ad libitum feeding and total excreta collection between 18 and 21 days of age.

a. Material and Methods

Birds: Breed and Breeding Conditions

Day old male Ross broilers are reared in collective battery cages till 12 days of age. They are fed a standard starter diet. At day 12, birds are weighed and equally distributed into 10 individual cages per treatment and were then fed the experimental diets for the adaptation period (minimum 5 days). Standard temperature and humidity programs are applied. The lighting program is kept constant 23 hours light and 1 hour darkness up to the end of the trial.

Feeds: Birds received a starter diet from day old to 12 days of age and then the experimental feeds.

Experimental Diets

Feeds contained 50% wheat and 22% barley (Table 1.1). Enzymes Preparation was sprayed onto 20 kg of crumbles.

In-feed enzyme recoveries are measured by viscometric method (Sabatier and Fish, 1996).

Measurement of Metabolizable Energy

The balance starts D18 according to the following procedure:

D 17, birds were fasted overnight;

D 18, birds weighing, clean collection trays;

D 19, faeces were collected and frozen;

D 20, faeces were collected and frozen, overnight fast;

D 21, faeces were collected and frozen, birds weighed and refed.

Faeces are then freeze-dried and ground as feed (1 mm, Retsch grinder). Gross energy of feed and excreta are measured on an IKA C5000 adiabatic calorimeter. Protein (N*6.25, Kjeldahl method Z130) and lipid (method Z160) contents are also determined. Correction for nitrogen balance was applied using 18% protein in the weight gain.

b. Results and Discussion

Apparent Metabolisable Energy Corrected for Nitrogen Balance ($AME_N$)

Zootechnical performances and Metabolisable Energy are presented Table 1.2. There was no difference in zootechnical performances between treatments.

In growing broilers, Enzymes Preparation improves $AME_N$ of a 50% wheat and 22% barley-based diet by 6.2% (+204 kcal/kg DM (Dry Matter)). Moreover, variability in energy digestibility was decreased from 80 to 62 kcal.kg DM.

This high improvement demonstrates the interest of both activities (xylanase and β-glucanase) produced by *Penicillium funiculosum* to hydrolysed soluble non starch polysaccharide of wheat and barley.

TABLE 1.1

Main ingredients and analysed characteristics of experimental diets

| Composition (%) | | |
|---|---|---|
| Wheat | 50 | |
| Barley | 22 | |
| Canola meal | 8 | |
| Poultry meal | 5 | |
| Soybean meal | 5 | |
| Meat meal | 5 | |
| Fat | 3 | |
| Vitamins/minerals | 2 | |
| **Characteristics (%)** | **Control** | **Enzymes** |
| DM | 89.7 | 89.6 |
| Crude Protein | 20.8 | 20.7 |
| Fat | 5.4 | 5.6 |

TABLE 1.2

Effect of Enzymes Preparation produced by *Penicillium funiculosum* on growth performance and apparent metabolizable energy in broilers receiving a 50% wheat and 22% barley-based diet.

| | Control n = 10 | Enzymes n = 10 |
|---|---|---|
| Dietary Gross Energy (kcal/kg DM) | 4609 | 4651 |
| Body Weight gain (g) | 156 ± 19.8 | 154 ± 22.3 |
| Feed intake (g/day) | 104 ± 15.8 | 99.7 ± 10.1 |
| FCR (g/g) | 1.99 ± 0.11 | 1.95 ± 0.17 |

TABLE 1.2-continued

Effect of Enzymes Preparation produced by *Penicillium funiculosum* on growth performance and apparent metabolizable energy in broilers receiving a 50% wheat and 22% barley-based diet.

| | Control n = 10 | Enzymes n = 10 |
|---|---|---|
| Fecal DM (%) | 34.7 ± 3.7 | 35.6 ± 8.3 |
| $AME_N$ (kcal/kg DM) | 3252 ± 80 | 3456 ± 62 |
| $AME_N$ (kcal/kg) | $2913^a$ ± 71.9 | $3095^b$ ± 55 |

EXAMPLE 2

Effect of Enzymes Preparation Produced by *Penicillium funiculosum* on Feed Digestibility in Wheat-fed Broilers The trial was performed to determine the effect of Enzymes Preparation produced by *Penicillium funiculosum* (activity of β-glucanase: 100 $U.kg^{-1}$ and activity of xylanase: 1100 $U.kg^{-1}$) on Apparent Metabolisable Energy (AME), protein and lipid digestibilities in broilers fed a diet containing 54% wheat. The interaction with grinding was also investigated.

(1) Control 1 (54% ground wheat)

(2) Control 1+Enzymes Preparation (activity of β-glucanase: 100 $U.kg^{-1}$ and activity of xylanase :1100 $U.kg^{-1}$)

(3) Control 2 (30% whole wheat, 24% ground wheat)

(4) Control 2+Enzymes Preparation (activity of β-glucanase: 100 $U.kg^{-1}$ and activity of xylanase: 1100 $U.kg^{-1}$)

according to the European Reference method (ad libitum feeding and total excreta collection from 18 to 21 days of age) (Bourdillon et al., 1990).

a. Material and Methods

Birds: Breed and Breeding Conditions

Day-old Ross male chicks are reared in collective battery cages up to 12 days of age. They are then transferred to individual battery cages for digestive balance. Standard temperature and humidity programs are applied. The lighting program was 23 hours light and 1 h darkness up to 8 days of age. It was then modified to 15h30 light, 8h30 darkness due to a layer trial run in the same building. Feeds: Birds received a standard starter diet up to 12 days of age and then the experimental feeds.

Experimental Diets

Experimental diets contained 54% wheat. Characteristics are given Table 2.1. Diet composition is reported Table 2.2.

Measurement of Apparent Metabolisable Energy

The balance starts on Day 17 according to the following schedule:

D 17, birds were fasted overnight;

D 18, birds weighing, clean collection trays;

D 19, feces were collected and freezed;

D 20, feces were collected and freezed, overnight fast;

D 21, feces were collected and freezed, birds weighed and refed.

Feces are then freeze-dried and ground as feed (1 mm, Retsch grinder). Gross energy of feed and excreta are measured on an IKA C5000 adiabatic calorimeter. Protein (N*6.25, Kjeldahl method Z130 for feeds and Z135 for feces) and lipid (method Z160) contents are also determined.

An amino acid profile is also performed by HPLC (method Z100 for feeds and Z080 for feces). Phosphorus content of feeds and excreta was measured using the AFNOR i method (NFV18-106).

b. Results and Discussion

Apparent Metabolisable Energy (AME)

Growth performance and metabolisable energy data are presented Table 2.3. Performance (weight gain, feed intake), measured over the three day period, did not differ between treatments. AME of the control diet containing 54% ground wheat was 3173 kcal/kg. Metabolisable energy of the diet containing the same total amount of wheat but of which 30% is as whole grain, is increased by 100 kcal/kg compared with the theoretical value. Moreover, variability appreciated by the standard deviation of the different criterions measured is also reduced with whole wheat.

Enzymes produced by *Penicillium funiculosum* (activity of β-glucanase: 100 $U.kg^{-1}$ and activity of xylanase: 1100 $U.kg^{-1}$) enhances metabolisable energy value of a 54% wheat-based diet by +3.4% (122 kcal/kg DM) if all wheat is ground and by +2.7% (101 kcal/kg DM) if 30% of the wheat is included as whole grains.

Apparent Digestibility of Nutrients (Lipids, Proteins and Amino Acids)

When all wheat is ground, apparent lipid and protein digestibilities are increased by 7 and 2.7% respectively, with Enzymes Preparation of *Penicillium funiculosum*. With part of the wheat as whole grains, the increase is less: +3 and +0.6% respectively, due to an overall enhanced nutrient digestibility. Indeed, nutrient digestibility with control diet containing whole wheat was similar to that of the experimental diet containing only ground wheat but supplemented with Enzymes Preparation.

Enzymes Preparation effects on apparent amino acid digestibility is presented Table 2.4. The improvement with Enzymes Preparation reaches on average +2.9% with all wheat as ground wheat and +1.1% with whole grains, confirming the effect on apparent protein digestibility.

Apparent Phosphorus Retention and Phosphorus Excretion

Enzymes preparation effect on apparent phosphorus retention is presented Table 2.5. Apparent phosphorus retention is significantly increased with Enzymes Preparation addition: +8.0%. This increase is greater than those observed for the other nutrients (+2.9 to +3.5% depending on the criterion : AME, proteins, lipids, amino acids). Such an increase might thus result from improved nutrient digestibility (direct effect of xylanase and β-glucanase) but also from a better action of the wheat phytase. When hydrolyzing non starch polysaccharides's, xylanase and β-glucanase give more accessibility to phytic acid for the endogenous wheat phytase.

This better digestive utilisation of phosphorus thus reduces phosphorus excretion: −8% when expressed as g phosphorus per kg weight gain.

TABLE 2.1

Wheat characteristics (%)

| % | Wheat |
|---|---|
| Dry Matter | 86.2 |
| Crude Protein | 10.87 |
| Lipids | 1.65 |
| β-Glucans | 0.77 |
| Pentosans | 6.8 |
| Relative Viscosity (mPa.s) | pH = 4.5:1.34<br>pH = 1.5:1.29 |

TABLE 2.2

Composition and Characteristics of experimental diets

| Diet | ground wheat | whole wheat |
|---|---|---|
| Composition (%) | | |
| Ground wheat | 53.84 | 23.84 |
| Whole wheat | 0 | 30.0 |
| Animal Fat | 3.52 | 3.52 |
| Soybean meal 48 | 18.26 | 18.26 |
| Meat & Bone Meal | 5.64 | 5.64 |
| Pea | 7.0 | 7.0 |
| Whole Rapeseed | 10.0 | 10.0 |
| vitamins/minerals | 1.74 | 1.74 |
| Characteristics (%) | | |
| ME (kcal/kg) | 3173 | 3.188 |
| Protein | 20.6 | 20.5 |
| Fat | 9.6 | 9.6 |
| Lysine | 1.05 | 1.04 |
| Methionine | 0.45 | 0.45 |
| Met + Cys | 0.85 | 0.85 |
| Calcium | 0.90 | 0.90 |
| Available P | 0.35 | 0.35 |

TABLE 2.3

Effect of Enzymes Preparation (activity of β-glucanase: 100 $U.kg^{-1}$ and activity of xylanase: 1100 $U.kg^{-1}$) on AME of a wheat-based diet (54% ground wheat or 24% ground + 30% whole wheat) in growing broilers.

| | Diets | | | |
|---|---|---|---|---|
| | 1<br>Ground wheat | 2<br>Ground wheat + Enzymes | 3<br>Whole wheat | 4<br>Whole wheat + Enzymes |
| Weight Gain (g) | 172 ± 11.8 | 170 ± 13.1 | 167 ± 8.9 | 165 ± 12.0 |
| Feed Intake (g) | 282 ± 20.5 | 272 ± 17.2 | 274 ± 15.5 | 267 ± 14.0 |
| Daily Feed intake (g/day) | 94 ± 6.8 | 91 ± 5.7 | 91 ± 5.2 | 89 ± 4.7 |
| FCR[3] (g/g) | 1.64 ± 0.05 | 1.60 ± 0.06 | 1.64 ± 0.05 | 1.63 ± 0.09 |

TABLE 2.3-continued

Effect of Enzymes Preparation (activity of β-glucanase: 100 $U.kg^{-1}$ and activity of xylanase: 1100 $U.kg^{-1}$) on AME of a wheat-based diet (54% ground wheat or 24% ground + 30% whole wheat) in growing broilers.

| | Diets | | | |
|---|---|---|---|---|
| | 1 Ground wheat | 2 Ground wheat + Enzymes | 3 Whole wheat | 4 Whole wheat + Enzymes |
| Apparent Protein Digestibility (%) | 83.8 ± $1.08^a$ | 85.9 ± $1.14^b$ | 86.5 ± $0.77^{bc}$ | 87.0 ± $0.80^c$ |
| Apparent Lipid Digestibility (%) | 82.2 ± $2.5^a$ | 88.0 ± $2.1^{bc}$ | 86.6 ± $2.45^b$ | 89.2 ± $1.25^c$ |
| AME (kcal/kg DM) | 3577 ± $76^a$ | 3699 ± $85^b$ | 3678 ± $35^b$ | 3779 ± $34^c$ |
| (kcal/kg) | 3194 ± 67 | 3303 ± 76 | 3284 ± 31 | 3375 ± 31 |

1: one-way analysis of variance. diet effect, n = 47; [a, b]values followed with the same superscript letters do not differ at $p < 0.05$.
2: two-way analysis of variance, n = 47 (wheat: 54% ground or 24% ground + 30% whole; enz: without or with 0.2 l/t Xylan).
[3]FCR: Feed Conversion Ratio (g feed:g gain)

TABLE 2.4

Effect of Enzymes Preparation on apparent digestibility of amino acids (%) of a 54% wheat based diet in growing broilers (one sample of mixed excreta per treatment)

| | Ground Wheat | | Ground + Whole Wheat | |
|---|---|---|---|---|
| | Témoin | Enzymes Preparation | Témoin | Enzymes Preparation |
| Nitrogen | 83.4 | 85.3 | 86.4 | 87.1 |
| ASP | 78.6 | 80.9 | 82.1 | 82.7 |
| THR | 74.2 | 75.3 | 78.0 | 79.9 |
| SER | 79.5 | 82.1 | 83.0 | 83.3 |
| GLU | 87.9 | 89.6 | 80.7 | 91.4 |
| PRO | 84.8 | 87.1 | 87.7 | 88.7 |
| GLY | 77.1 | 79.9 | 80.7 | 82.0 |
| ALA | 74.6 | 76.9 | 78.2 | 80.1 |
| VAL | 78.6 | 80.8 | 81.8 | 83.0 |
| ILE | 80.6 | 83.0 | 84.0 | 85.0 |
| LEU | 82.1 | 84.3 | 85.3 | 86.4 |
| TYR | 80.9 | 85.0 | 83.7 | 84.4 |
| PHE | 83.7 | 85.9 | 87.1 | 87.6 |
| LYS | 80.6 | 83.1 | 83.9 | 84.8 |
| HIS | 81.7 | 84.9 | 85.0 | 86.0 |
| ARG | 84.9 | 87.6 | 88.1 | 89.0 |
| CYS | 70.8 | 72.8 | 76.5 | 77.0 |
| MET | 87.2 | 88.5 | 88.5 | 89.4 |
| TRP | 79.5 | 82.7 | 83.3 | 84.7 |

TABLE 2.5

Effect of Enzymes Preparation on phosphorus (P) excretion and apparent retention of phosphorus of wheat-based diet (54% ground wheat) in growing broilers (n = 12)

| Diets | 1 Wheat | 2 Wheat - Enzymes preparation | Enzyme effect p |
|---|---|---|---|
| Apparent P Retention (%) | 37.9 + 3.0 | 40.5 ± 2.8 | 0.047 |
| Excreted P (g/bird/3 days) | 1.24 ± 0.13 | 1.14 ± 0.1 | 0.071 |
| P Excretion (g/kg gain) | 7.2 ± 0.5 | 6.7 ± 0.5 | 0.034 |

EXAMPLE 3

Evaluation of Enzymes Preparation on $AME_N$ of a Wheat Based Diet in Growing Turkeys The aim of this assay is to demonstrate the efficacy of Enzymes Preparation from *Penicillium funiculosum* (activity of β-glucanase: 100 $U.kg^{-1}$ and activity of xylanase: 1100 $U.kg^{-1}$) on Apparent Metabolizable Energy (AME) of a wheat-based diet according to the following experimental design:

(1) Control;

(2) EP 1: Enzymes Preparation (activity of β-glucanase 100 $U.kg^{-1}$ and activity of xylanase: 1100 $U.kg^{-1}$);

(3) EP 2: Enzymes Preparation (activity of β-glucanase 150 $U.kg^{-1}$ and activity of xylanase 1650 $U.kg^{-1}$);

using the European Reference Method (Bourdillon et al., 1990) with ad libitum feeding and total excreta collection between 33 and 37 days of age.

a. Material and Methods

Birds: Breed and Breeding Conditions

Day old male BUT9 turkeys were reared in collective battery cages up to 20 days of age. They were then transferred to individual battery cages for the digestibility balance after an adaptation period of at least 7 days. Standard temperature and humidity programmes were applied. The lighting program was kept constant 23 hours light and 1 hour darkness for the 2 first weeks and then reduced to 15 hours light for 9 hours darkness up to the end of the trial. Feeds: Birds received a standard complete starter diet from day-old to 21 days of age and then the experimental feeds.

Experimental Diets

Feeds contained 47% wheat and 33% soybean meal (Table 3.1). Enzyme spraying was done in on 20 kg pellets of control diets.

Measurement of Metabolizable Energy

At D 21, birds were weighed and equally distributed in 10 individual cages per treatment and were then fed the experimental diets.

The balance starts D 33 according to the following procedure

D 32, birds were fasted overnight;

D 33, birds weighing, clean collection trays;

D 34 and D 35, feces were collected and freezed;

D 36, feces were collected and freezed, overnight fast;

D 37, feces were collected and freezed, birds weighed and refed.

Feces are then freeze-dried and ground as feed (1 mm, Retsch grinder). Gross energy of feed and excreta are measured on an IKA C5000 adiabatic calorimeter. The AME is corrected for N balance by taking into account the body weight gain (g) and its nitrogen content (21% crude protein). Feces are then freeze-dried and ground as feed (1 mm, Retsch grinder). Gross energy of feed and excreta are measured on an IKA C5000 adiabatic calorimeter. Protein (N*6.25, Kjeldahl method Z130 for feeds and Z135 for feces) is also determined and an amino acid profile performed by HPLC (method Z100 for feeds and Z080 for feces).

b. Results and Discussion

Apparent Metabolisable Energy (AME)

Zootechnical performances and Metabolisable Energy are presented Table 3.2. There was no significant difference in growing performance during the balance between treatments.

In growing turkeys, Enzymes Preparation improves $AME_N$ of a wheat-based diet by 2.2 and 5.4% for EP 1 and EP 2 respectively.

The high improvement observed demonstrates the interest of both activities (xylanase and β-glucanase) contained in Enzyme Preparation to hydrolysed non starch polysaccharide of wheat for improving energy value of this cereal in growing turkeys.

TABLE 3.1

Main ingredients and analysed characteristics of experimental diets

| Composition (%) | | | |
|---|---|---|---|
| Wheat | 47.55 | | |
| Extruded soybean | 5.00 | | |
| Soybean meal | 33.00 | | |
| Meat meal | 6.00 | | |
| Fat | 4.00 | | |
| DiCalcium Phosphate | 2.30 | | |
| $CaCO_3$ | 0.85 | | |
| Vitamins/minerals | 1.30 | | |
| **Characteristics (%)** | **Control** | **EP 1** | **EP 2** |
| DM | 89.0 | 89.1 | 88.9 |
| Crude Protein | 26.3 | 26.1 | 26.3 |
| Fat | 6.4 | | |

EXAMPLE 4

Evaluation of Enzymes Preparation Produced by *Penicillium funiculosum* Efficacy of Wheat-based Complete Feed Diet in Growing Pigs The objective is to evaluate the effect of enzyme supplementation of wheat-based diets on energy digestion in the small intestine of growing pigs. Enzymes Preparation normal level activity is 1100 $U.kg^{-1}$ for xylanase and 100 $U.kg^{-1}$ for β-glucanase.

a. Material and Methods

Animals

The treatments were tested according to a Latin square design with three diets and three periods and two pigs per diet* period. The diets were fed at fixed levels according to weight of pig throughout the period of the test.

Experimental Diet

A diet based on poor quality wheat and balanced with other typical feed ingredients was fed to six growing pigs (see table 4.1.). The diet was fed either:

1. Unsupplemented (basal);
2. Supplemented (1): with Enzymes Preparation at 1× level (activity of β-glucanase: 100 $U.kg^{-1}$ and activity of xylanase: 1100 $U.kg^{-1}$);
3. Supplemented (2): with Enzymes Preparation at 2× level (activity of β-glucanase: 200 $U.kg^{-1}$ and activity of xylanase: 2200 $U.kg^{-1}$);

Accurate dosing of the diet was achieved by diluting the Enzymes Preparation with corn starch to create a premix which was then added to the diet as appropriate.

Sample Collection

Ileal juices were collected for a period of 48 hours each week according to standard procedures at the RPNA laboratories. A sample of the ileal juice and of the test diets were analysed for energy by bomb calorimetry by Sanders to determine digestible energy. Aliquots of the samples were stored for further analysis if necessary.

Statistical Analysis

Digestibility of the crude energy was calculated from the results of the bomb calorimetry of the ileal juices, feed and

TABLE 3.2

Effect of Enzymes Preparation on apparent metabolizable energy corrected for nitrogen balance ($AME_N$) of a wheat-based diet in growing turkeys (32 to 37 days). (means ± SD)

| | Control n = 12 | EP 1 n = 12 | EP 2 n = 12 | probability[1] enzyme effect | probability[1] dose effect |
|---|---|---|---|---|---|
| Gross Energy (kcal/kg DM) | 4659 | 4680 | 4654 | | |
| Body Weight gain (g) | 341 ± 23 | 338 ± 36 | 337.5 ± 57 | NS | NS |
| Feed intake (g/day) | 111 ± 5.9 | 107 ± 6.3 | 103 ± 12.1 | NS | NS |
| Feed Conversion Ratio (g/g) | 1.63 ± 0.09 | 1.60 ± 0.12 | 1.59 ± 0.17 | NS | NS |
| Fecal DM (%) | 26.1 ± 5.5 | 26.5 ± 2.2 | 25.9 ± 4.8 | NS | NS |
| $AME_N$ (kcal/kg DM)[2] | 3025 ± 86 | 3092 ± 56 | 3191 ± 34 | 0.037 | 0.061 |
| $AME_N$ (kcal/kg)[2] | 2700 ± 77 | 2753 ± 50 | 2840 ± 30 | 0.037 | 0.061 |

[1]One-way analysis of variance: Enzyme effect: n = 60, a,b: means not followed by the same letter are significantly different at $p < 0.05$; Dose effect: 0, 0.2, 0.3 l/t.
[2]Mean ± SEM feed intakes. Analysis of variance was undertaken on the digestibility calculations.

TABLE 4.1

Ingredient and nutrient specification of the basal diet

| | Percentage inclusion |
|---|---|
| Ingredients | |
| Wheat | 60.0 |
| Barley | 9.7 |
| Peas | 11.4 |
| Fish meal | 5.0 |
| Sunflower meal (30) | 10.0 |
| Lysine | 0.15 |
| Minerals and vitamins | 3.75 |
| Total | 100.0 |
| Nutrients | |
| Protein | 14.9 |
| Dry matter | 84.9 |
| Digestible Energy (kcal/kg) | 3150 |
| Fibre | 5.1 |
| Dig. lysine | 0.8 |

b. Results and Discussion

The xylanase supplementation of diets of pigs increased the energy digestibility by at least six per cent. This indicates that the enzyme is increasing the breakdown of the raw material cell walls (in particular, wheat) and the release of additional energy in the small intestine.

TABLE 4.2

Effect of Enzyme Preparation supplementation of Wheat-based diets on the energy digestibility of feeds given to growing pigs.

| | Un-supplemented treatment | Supplemented (1) | Supplemented (2) | p value |
|---|---|---|---|---|
| Mean (%) | 70.1 | 74.5 | 75.6 | <0.001 |
| Energy digestibility | 0.80 | 0.49 | 0.45 | |
| % improvement | | 6.27 | 7.87 | |

EXAMPLE 5

Effect of Enzymes Preparation Produced by *Penicillium funiculosum* on Performance of Straw, Corn Silage, Hay and Grass Silage Diets in Ruminants HFT test (Hohenheimer Futterwertesten, Menke et al., 1979, 1988) is an in vitro incubation test allowing the measure of raw material degradation through the gas volume produced by the fermentation of these fedstuffs in a buffered rumen juice.

a. Material and Methods 200 mg of dried and ground substrate is incubated with 10 ml of rumen juice plus 20 ml of buffer in syringes which are gently agitated on a rotor in a temperature controlled incubator (39° C.). Volume of gas produced are registered at 24 hours. Blank (without substrate), standard hay control and standard concentrate control (with known value of net gas volume production) are used to correct the results and calculate a net volume of gas produced in 24 hours. The energy value and OMD (Organic Matter Digestibility) of substrates are calculated using volume of gas produced in 24 hours and predictor equations proposed by Menke et al. (1988).

Rumen juice is collected on 2 dry cows, rumen canulated and fed at 8 a.m. and 7 pm with a ration composed with 6 kg hay and 2 kg concentrate (ratio 75/25). Rumen juice collect is realized just before a.m. feeding. Rumen juice is filtered to avoid alimentary particules passage and is maintained in strict anaerobic conditions.

The aim of this trial was to test the effect of Enzymes Preparation application on the forage 15 hours before HFT incubation.

Pretreatment with Enzymes Preparation: the enzyme solution is spraid on the forage on the floor on straw, corn silage, hay and grass silage. Spraying is realized with 1 ml of Enzymes Preparation onto 2 kg forage dry matter. Forage at the edge (about 10 cm) is rejected to improve the homogeneity of the sample. After treatment, the forage is mixed by hand and left at room temperature for 15 hours after spraying. HFT incubation is carried out after 15 hours Enzymes Preparation contact through one serie and 6 replicates per treatment.

b. Results and Discussion

Net gas volume production at 24 hours is given in the table 5.1 for straw, corn silage, hay and grass silage.

Application of cellulase on straw through pretreatment gives a 18% net volume of gas improvement vs. control. For corn silage, this improvement is 8%, for hay, 9.5% and for grass silage 9%.

OMD is given in the table 5.2, for the different forage before and after pretreatment.

OM digestibility is respectively improved for straw, corn silage, hay and grass silage vs. control: 8.5% straw, 5% corn silage, 5.4% hay and 5% grass silage.

15 hours pretreatment of forages (straw, corn silage, hay, grass silage) with Enzyme Preparation improves intensity of rumen substrate incubation and OM digestibility of substrate.

TABLE 5.1

Net gas volume production at 24 hours

| RAW MATERIAL | TREATMENT | NET GAS VOLUME (at 24 hours) | Stat Sign |
|---|---|---|---|
| STRAW | Control | 25 | S ($p < 0.05$) |
| | Cellulase | 29,5 | |
| CORN SILAGE | Control | 53,7 | S ($p < 0.05$) |
| | Cellulase | 57,8 | |
| HAY | Control | 39,5 | ($p < 0,08$) |
| | Cellulase | 43,1 | |
| GRASS SILAGE | Control | 43,7 | ($p < 0,08$) |
| | Cellulase | 47,7 | |

TABLE 5.2

OMD

| RAW MATERIAL | TREATMENT | OMD | σ | Stat sign |
|---|---|---|---|---|
| STRAW | Control | 47,0 | 0,67 | S ($p < 0,05$) |
| | Cellulase | 51,0 | 2,37 | |
| CORN SILAGE | Control | 70,7 | 0,91 | S ($p < 0,05$) |
| | Cellulase | 74,2 | 2,19 | |
| HAY | Control | 59,7 | 0,77 | $p < 0,08$ |
| | Cellulase | 62,9 | 3,27 | |
| GRASS SILAGE | Control | 70,5 | 0,72 | $p < 0,08$ |
| | Cellulase | 74,0 | 3,46 | |

EXAMPLE 6

Effect of Enzymes Preparation Produced by *Penicillium funiculosum* on Performance of Wheat or Barley-fed Layers The purpose of this experiment was to evaluate the effects of Enzymes Preparation addition on productive parameters of laying hens fed with wheat or barley-based diets.

a. Material and Methods

Experiment Design 4 treatments×8 replicates×5 cages×3 hens

Treatments:

1. Control 1: 60% wheat
2. Control 1+Enzymes Preparation
3. Control 2: 60% barley
4. Control 2+Enzymes Preparation Animals, Housing and Management The trial was conducted on four hundred and eighty brown hens of the Hy-Line strain. Each replicate was formed by five pens, with a common feeder, i.e. a total of thirty-two replicates of fifteen birds each. Distributed in two identical rooms, the replicates had programmable lights and ventilation. The lighting program started with 14 hours of light per day on arrival of hens at 17 weeks of age, increasing every two weeks by 30 minutes, up to a maximum of 17 hours of light per day. Hens were 22 weeks old at the beginning of the experiment, that lasted during the first five months of laying period.

Diets and Feeding

There were two experimental diets based on 60% of wheat (diet 1) and 60% of barley (diet 2), and 10% of sunflower meal. Their composition is shown in Table 6.1. Cereals characteristics are presented Table 6.2.

Controls

Chemical Analysis:

Feed Samples

Quality control of experimental feeds was performed by analyzing dry matter, crude protein, crude fat and ash. Xylanase activity (T-1, T-2) and β-glucanase activity (T-3, T-4) were determined in mash feeds.

Measurements

Feed consumption and feed efficiency were recorded every four weeks. Hens were weighed at the beginning and at the end of the experiment. Egg production, egg weight and percentage of dirty and faulty eggs were recorded daily, during five periods of four weeks each. Mortality was checked and recorded daily, including the cause of death.

b. Results and Discussion

Performance Trial

The productive parameters obtained during the trial are shown in Tables 6.3 to 6.5. In the first two periods (from week 22 to 30) and in the overall experiment the percentage of dirty eggs was statistically affected by treatment (P>0.005). Animals fed wheat diet without enzyme produced more dirty eggs. Statistically significant differences between treatments were found in egg laying percentage (P>0.05) and in egg weight (P>0.005) from second period to the end of experiment. Animals fed barley diets presented higher egg laying percentage and produced heavier eggs than animals fed wheat diets. Enzymes Preparation seem to increase these parameters but not significantly at 0.05 level of probability. In all experimental periods, feed intake of animals from treatments T-3 and T-4 (barley diets) was higher than consumption of animals fed wheat diets, due to the energy levels of both diets (barley diets were formulated at 2600 kcal/kg of energy while wheat diets contained 2800 kcal/kg). Taking into account the different energy values of both types of diets and feed consumption of animals, in the overall period all animals presented the same daily energy consumption.

The feed efficiency (expressed as g feed/g egg) of experimental diets during the first period was very high due to the low egg laying rate of hens during this period of time. In the first two periods, feed efficiency for wheat treatments was better than those obtained with barley treatments; but in third period, when highest egg laying percentages were recorded, both types of diets presented similar efficiencies. From week 34 to the end of experiment, barley diets presented better feed efficiencies than treatments with wheat. Enzyme tends to improve feed efficiency (P>0.05). In the overall period β-glucanase improved feed efficiency of barley diet (with a P=0.066).

Table 6.4 shows that wheat-fed layers supplemented with Enzymes Preparation tend to exhibit higher laying rates (+1.5 absolute points), greater mean egg weight (+0.37 g) and lower Feed Conversion Ratio (−2.7%) than unsupplemented ones.

Table 6.5 shows that Enzyme Preparation addition to barley-fed layers improved laying rate (+4%), mean egg weight (+0.7%) and Feed Conversion Ratio (−5.7%) compared with control barley diets.

TABLE 6.1

Composition of experimental laying diets

| Ingredient | Wheat diet | Barley diet |
|---|---|---|
| Wheat | 60.171 | — |
| Barley | — | 59.033 |
| Animal and vegetal fat (30% linoleic acid) | 4.0 | 4.0 |
| Full fat extruded soybean | 11.412 | 10.399 |
| Soybean meal, 48% | 3.443 | 5.705 |
| Sunflower meal, 29% | 10.0 | 10.0 |
| DL-methionine | 0.091 | 0.101 |
| L-lysine HCl | 0.111 | — |
| Calcium Carbonate | 8.595 | 8.546 |
| Dicalcium phosphate | 1.478 | 1.517 |
| Salt | 0.30 | 0.30 |
| Mineral and vitamins premix* | 0.40 | 0.40 |
| Estimated nutritive value | | |
| Metabolizable energy (kcal/kg) | 2800 | 2600 |
| Crude protein | 16.0 | 16.41 |
| Crude fat | 7.48 | 7.21 |
| Lysine | 0.75 | 0.76 |
| Methionine | 0.35 | 0.35 |
| Methionine + cysteine | 0.67 | 0.69 |
| Calcium | 3.70 | 3.70 |
| Inorganic phosphorus | 0.40 | 0.40 |
| Sodium/Chloride | 0.16/0.27 | 0.15/0.29 |

(*) one kilo of feed contains: Vitamine A 8000 UI; Vitamin D3: 1600 UI; Vitamin E: 5 mg; Vitamin K3: 2 mg; Vitamin B1: 1.5 mg; Vitamin B2: 4 mg; Vitamin B6: 3 mg; Vitamin B12: 11.8 μg; Folic acid: 0.35 mg; Biotin: 150 μg; Calcium Pantotenate: 10 mg; Nicotinic acid: 20 mg; Mn: 30 mg; Zn: 50 mg; I: 0.3 mg; Fe: 50 mg; Cu: 6 mg; Se: 0.1 mg; Etoxiquin: 125 mg.

TABLE 6.2

Analytical composition of cereals

| Parameter | Percentage | |
|---|---|---|
| | Wheat (970556) | Barley (970287) |
| Moisture | 10.65 | 9.79 |
| Ash | 1.57 | 2.11 |
| Crude fat | 1.76 | 1.98 |
| Crude fibre | 2.43 | 4.61 |
| Crude protein | 10.65 | 10.55 |
| Viscosity (pH 1.5 with inactivation, in cps) | 0.78 | 2.31 |
| Total β-glucans (% DM) | 0.66 | 3.57 |
| Insoluble β-glucans (% DM) | 0.50 | 1.56 |
| Total pentosans | 4.91 | 8.75 |
| Soluble pentosans | 0.51 | 0.39 |

TABLE 6.3

Productive parameters from 22 to 42 weeks (complete experimental protocol)

| Treatment | Egg laying %[1] | Dirty eggs % | Faulty eggs (%) | Egg Weight (g) | Feed intake (g) | Feed efficiency (l) | Animal weight gain (g) | Mortality (%) |
|---|---|---|---|---|---|---|---|---|
| T-1 | 75.6b | 7.9a | 0.8 | 62.29b | 101.5b | 2.158 | 219.8 | 1.7 |
| T-2 | 77.1b | 6.6ab | 1.1 | 62.66b | 101.5b | 2.100 | 222.6 | 0.8 |
| T-3 | 78.0ab | 5.3b | 1.0 | 63.76a | 109.4a | 2.203 | 231.8 | 2.5 |
| T-4 | 81.2a | 6.6ab | 1.0 | 64.22a | 110.0a | 2.111 | 227.7 | 5.0 |
| | 1.3 | 0.4 | 0.2 | 0.4 | 1.5 | 0.028 | 16.8 | 1.4 |
| Treatment Effect (P) | 0.0402 | 0.0039 | 0.7796 | 0.0036 | 0.0003 | 0.0659 | 0.9586 | 0.2645 |

[1]comparison with a genetically perfect hens (value given by hens supplier).
Values are means of eight replicates of 15 hens. Within columns, means followed by a different superscript are significantly different ($P < 0.05$).

TABLE 6.4

Effect of Xylan on laying performance of wheat-fed layers (in absolute values[1] and percentage[2] compared with control)

| Weeks | Laying rate (%)[1] | | Egg weight (g)[1] | | Feed Conversion Ratio 1 | Feed Conversion Ratio 2 |
|---|---|---|---|---|---|---|
| 22–26 | +1.0 | | −0.3 | | +0.067 | −1.9% |
| 26–30 | +1.1 | | +0.7 | | −0.098 | −4.7 |
| 30–34 | +1.4 | | +0.8 | | −0.039 | −2.0 |
| 34–38 | +2.1 | | +0.6 | | −0.039 | −2.0 |
| 38–42 | +2.3 | | −0.5 | | −0.042 | −2.2 |
| Overall | +1.5 | +2.0% | +0.37 | +0.6% | −0.058 | −2.7% |

3. For the 22–42 week period

TABLE 6.5

Effect of Enzymes Preparation on laying performance of barley-fed layers (in absolute values[1] and percentage[2] compared with control)

| Weeks | Laying rate (%)[1] | | Egg weight (g)[1] | | Feed Conversion Ratio 1 | Feed Conversion Ratio 2 |
|---|---|---|---|---|---|---|
| 22–26 | +3.7 | | +1.0 | | −0.381 | −9.0% |
| 26–30 | +3.0 | | +0.5 | | −0.137 | −6.3 |
| 30–34 | +1.9 | | +0.5 | | −0.015 | −0.8 |
| 34–38 | +3.3 | | +0.6 | | −0.067 | −3.5 |

TABLE 6.5-continued

Effect of Enzymes Preparation on laying performance of barley-fed layers (in absolute values[1] and percentage[2] compared with control)

| Weeks | Laying rate (%)[1] | | Egg weight (g)[1] | | Feed Conversion Ratio 1 | Feed Conversion Ratio 2 |
|---|---|---|---|---|---|---|
| 38–42 | +0.9 | | +0.3 | | −0.082 | −4.2 |
| Overall | +3.2 | +4% | +0.46 | +0.7% | −0.092 | −5.7% |

[3]For the 22–42 week period

Bibliography

Bourdillon A., Carré B., Conan L., Duperray J., Franscesch M., Fuentes M., Huyghebaert G., Jansen W.M.M.A., Leclercq B., Lessire M., McNab J., Rigoni M., Wiseman J., 1990. European reference method for the in vivo determination of metabolizable energy with adult cockerels: reproductibility, effect of age, comparison with predicted values. *British Poultry Science* 31, 567-576.

Sabatier A. M., Fish N. M. 1996. Method of analysis for feed enzymes: methodological problems? *Journal of Applied Poultry Research* 5, 408–413.

Barrier-Guillot B., Métayer J. P., Bouvarel I., Castaing J., Picard M., Zwick J. L. 1997. *Proceedings of the Xlth European Symposium on Poultry Nutrition*, WPSA, Aug 24–28th Faaborg, Denmark, 237–239.

Svihus B., Herstad O., Newman C. W., Newman R. K. 1997. *British Poultry Science* 38, 524–529.

SEQUENCE LISTING

<160> NUMBER OF SEQ ID NOS: 14

<210> SEQ ID NO 1
<211> LENGTH: 2898
<212> TYPE: DNA
<213> ORGANISM: Pennicilium funiculosum
<220> FEATURE:
<221> NAME/KEY: RBS
<222> LOCATION: (570)...(576)
<221> NAME/KEY: RBS
<222> LOCATION: (724)...(730)
<221> NAME/KEY: CDS
<222> LOCATION: (1317)...(1589)
<221> NAME/KEY: intron
<222> LOCATION: (1590)...(1642)
<221> NAME/KEY: CDS
<222> LOCATION: (1644)...(2042)

<400> SEQUENCE: 1

```
catccataca ggtttctcct gtatggaatt tgtaattact tatcactaat tgtcacaatt     60

ctcaggtttt ctgaacatgc tttcttttcc gtccggcatt gttaagcttg atcatagcct    120

gtgtttctta aaggcggttc cggcggtaat ctcagtacta cgtcctacgt atgtaggtag    180

ttatatctat cctacccttt gactgtatgt tccctacttt gcagtactta gacaacgatt    240

ttctaggcag gttcctagaa tgctctcgtt ttcgtttact atcattgttt ttatgcgcgt    300

aatgtggagc tattgacgtg tatgtcactt tacatgccta taactaactt aatctaaacg    360

tccattaggg gttcaacata tgtattcccc gcctccgcat gttcactcca atgtggaaat    420

tatctccacc gtgcccaaca cttccctgat aatgagcaat gtcgatgagt atttcaatgc    480

aagaatctga gccgaatcaa gttttacaag gttagtcatt ggttgatcct gttgtcgaaa    540

gctagtgcag gttatgctcc gccgatgaag gctaaatata taacgggaga taaccctaac    600

tacctaggta tcaacccaac gcgacattga aaaatcttca aaaacatcct tactagcgga    660

tatcaatagc gagaactgcg attaaacatt gtcgatcttc ggcactttag cagcatgact    720

tcaggctaaa cacattgatg caaaccgctt tctcatttta cctgaaactt gggatgacga    780

atcctccaac cagttgtcga aacgaacagg ctccacatct cgcaacaaat caaagcaacg    840

agtctaatat atgtattcgt catctagtaa agatcaaacg atttcgtttc agcggtggta    900

catacccaa gcactccgac aagtcggtta tccagacctg tcgatcttga atatcgccca     960

tacagagctc ttctttaaag accacgaccg aacatcaagg agaatttagc cagaaatttt   1020

ccggtatgcg agaatgatcc cagatttgca acagaaaagt gctctattgc gaatatcctc   1080

aagcatattc cccgaaactc cgcgatggag accttgaggg gggtcatatg gatgcgaggc   1140

atgatgaaac aaacaacccg ttactgttaa atgagaaatg agaatgcggg tatataaaca   1200

tgcggattgt cctcgccaga aaatcccccc cccccccccc caccaaaaca aaagacgtac   1260

cactcatttt ctggatatcc acacttggcg agaatcaaag aaccatttca atcaag atg   1319
                                                              Met
                                                               1

aag ctc ttc cta gct gca att gtc ctt tgc gca act gcc gcg aca gcc     1367
Lys Leu Phe Leu Ala Ala Ile Val Leu Cys Ala Thr Ala Ala Thr Ala
            5                  10                  15

ttc cca tca gaa ctt gct caa cgc gct gcg gga gac ctt agc aag cgt     1415
Phe Pro Ser Glu Leu Ala Gln Arg Ala Ala Gly Asp Leu Ser Lys Arg
        20                  25                  30

caa tca atc acg acc agc cag act ggg acg aac aac ggc tac tac tac     1463
Gln Ser Ile Thr Thr Ser Gln Thr Gly Thr Asn Asn Gly Tyr Tyr Tyr
```

-continued

```
     35                  40                  45

tcg ttc tgg acc aac ggc gga gga gaa gtc act tac aca aat ggc gac     1511
Ser Phe Trp Thr Asn Gly Gly Gly Glu Val Thr Tyr Thr Asn Gly Asp
 50                  55                  60                  65

aat ggc gag tac agc gtg aca tgg gtc gat tgt ggt gac ttt aca tct     1559
Asn Gly Glu Tyr Ser Val Thr Trp Val Asp Cys Gly Asp Phe Thr Ser
                 70                  75                  80

ggc aag ggc tgg aat cca gcc aat gca cag taagtttccc tctttccttc       1609
Gly Lys Gly Trp Asn Pro Ala Asn Ala Gln
             85                  90

taagcttata ttgtacgtac tcacaatttg cagg act gtc acg tac tca gga gaa   1664
                                      Thr Val Thr Tyr Ser Gly Glu
                                                      95

ttt aac ccc tct gga aac gct tat ttg gct gtc tac ggg tgg aca aca     1712
Phe Asn Pro Ser Gly Asn Ala Tyr Leu Ala Val Tyr Gly Trp Thr Thr
    100                 105                 110

gat cct ctt gtc gaa tac tac atc ctg gag tcc tac ggc acc tat aac     1760
Asp Pro Leu Val Glu Tyr Tyr Ile Leu Glu Ser Tyr Gly Thr Tyr Asn
115                 120                 125                 130

cca tca tct gga ctt act tca ctt ggc cag gtc act agc gat ggt ggc     1808
Pro Ser Ser Gly Leu Thr Ser Leu Gly Gln Val Thr Ser Asp Gly Gly
                135                 140                 145

acc tac gat atc tac tca acc cag cgt gtc aac cag cct tcc att gag     1856
Thr Tyr Asp Ile Tyr Ser Thr Gln Arg Val Asn Gln Pro Ser Ile Glu
            150                 155                 160

gga act tcc acc ttc aac cag tac tgg tca gtt cgc acc gag aag cga     1904
Gly Thr Ser Thr Phe Asn Gln Tyr Trp Ser Val Arg Thr Glu Lys Arg
        165                 170                 175

gtc ggc gga act gtc acc acg gcc aac cac ttt gca gca tgg aag gca     1952
Val Gly Gly Thr Val Thr Thr Ala Asn His Phe Ala Ala Trp Lys Ala
    180                 185                 190

ctt gga ctt gaa atg ggc act tat aac tat atg att gtg tcc acc gaa     2000
Leu Gly Leu Glu Met Gly Thr Tyr Asn Tyr Met Ile Val Ser Thr Glu
195                 200                 205                 210

ggc tac gag agc agt ggc tct agt acc atc aca gtg tcc tag             2042
Gly Tyr Glu Ser Ser Gly Ser Ser Thr Ile Thr Val Ser  *
                215                 220

acatgtctca atgacgcttg ttacacagct gtccctttat tgacacttat aaatgactta   2102

tggaagggag tcggcaaaat ttttatgttc gaagtttcat atgtctattg tggaaatcgg   2162

cccatatttt cagggctagt cactctttga ttgcatctta agttacttga tcaaattaag   2222

ccctaacacc aagatctgga atgcgagcaa tatcaagtat ttattcattt attttaaacc   2282

ccggagtggg ctgtctttga tagtatagta atgatgcaca tttgttgtgg cagccttacc   2342

tgtttttcca ttggcattcg agatatctac cgacatgttc cttcagcaag cagtatttat   2402

cgcgtctcga tcaagcatcg acggcctttt ggggaaacca agaaaaatat tttggcctcc   2462

atatctctgt cgcacattcc ctccttctct gaaacctttg cttttgggaa cgttcgaaaa   2522

aacagagcgg ttgcaagcag tagctccatc caggcaagat gcataccgat gcatactagt   2582

gagtaggcca gttagcgaat tgtttgttct cagtgccgat gatgaaatta tgcaattaaa   2642

gacttactgc gagacccgcc accaaagggc atgaaaacat gcttcatctc ttttgtggga   2702

ttctcccatc tgcttggatc aaagctatat cccggacatc aatagttagc gatattgaat   2762

cgaacatctg ccatgccttg taggcgggaa agtgacaccg aataggctat aggaaccact   2822

cacgcatgag gattgggaaa cacatcaggg tcgcgatgta aagtatatgc ctgagtagat   2882

actgtgacac ctccag                                                   2898
```

-continued

```
<210> SEQ ID NO 2
<211> LENGTH: 223
<212> TYPE: PRT
<213> ORGANISM: Penicillium funiculosum

<400> SEQUENCE: 2

Met Lys Leu Phe Leu Ala Ala Ile Val Leu Cys Ala Thr Ala Ala Thr
 1               5                  10                  15

Ala Phe Pro Ser Glu Leu Ala Gln Arg Ala Ala Gly Asp Leu Ser Lys
            20                  25                  30

Arg Gln Ser Ile Thr Thr Ser Gln Thr Gly Thr Asn Asn Gly Tyr Tyr
        35                  40                  45

Tyr Ser Phe Trp Thr Asn Gly Gly Gly Glu Val Thr Tyr Thr Asn Gly
    50                  55                  60

Asp Asn Gly Glu Tyr Ser Val Thr Trp Val Asp Cys Gly Asp Phe Thr
65                  70                  75                  80

Ser Gly Lys Gly Trp Asn Pro Ala Asn Ala Gln Thr Val Thr Tyr Ser
                85                  90                  95

Gly Glu Phe Asn Pro Ser Gly Asn Ala Tyr Leu Ala Val Tyr Gly Trp
            100                 105                 110

Thr Thr Asp Pro Leu Val Glu Tyr Tyr Ile Leu Glu Ser Tyr Gly Thr
        115                 120                 125

Tyr Asn Pro Ser Ser Gly Leu Thr Ser Leu Gly Gln Val Thr Ser Asp
    130                 135                 140

Gly Gly Thr Tyr Asp Ile Tyr Ser Thr Gln Arg Val Asn Gln Pro Ser
145                 150                 155                 160

Ile Glu Gly Thr Ser Thr Phe Asn Gln Tyr Trp Ser Val Arg Thr Glu
                165                 170                 175

Lys Arg Val Gly Gly Thr Val Thr Thr Ala Asn His Phe Ala Ala Trp
            180                 185                 190

Lys Ala Leu Gly Leu Glu Met Gly Thr Tyr Asn Tyr Met Ile Val Ser
        195                 200                 205

Thr Glu Gly Tyr Glu Ser Ser Gly Ser Ser Thr Ile Thr Val Ser
    210                 215                 220


<210> SEQ ID NO 3
<211> LENGTH: 8
<212> TYPE: PRT
<213> ORGANISM: Artificial Sequence
<220> FEATURE:
<223> OTHER INFORMATION: Basis for the design of PCR primer sequences
      based on internal sequence

<400> SEQUENCE: 3

Tyr Ala Gly Thr Cys Asp Pro Asp
 1               5


<210> SEQ ID NO 4
<211> LENGTH: 9
<212> TYPE: PRT
<213> ORGANISM: Penicillium funiculosum

<400> SEQUENCE: 4

Ala Lys Tyr Gly Thr Gly Tyr Cys Asp
 1               5


<210> SEQ ID NO 5
<211> LENGTH: 285
```

-continued

```
<212> TYPE: DNA
<213> ORGANISM: Pennicium funiculosum
<220> FEATURE:
<221> NAME/KEY: CDS
<222> LOCATION: (1)...(285)
<221> NAME/KEY: primer_bind
<222> LOCATION: (1)...(27)
<221> NAME/KEY: primer_bind
<222> LOCATION: (264)...(285)

<400> SEQUENCE: 5

gcc aag tac ggt acg ggt tat tgt gac tct caa tgc cct cgt gac ttg       48
Ala Lys Tyr Gly Thr Gly Tyr Cys Asp Ser Gln Cys Pro Arg Asp Leu
 1               5                  10                  15

aag ttc atc gct ggt cag gcc aac gtc gag ggc tgg acg cct tcc acc       96
Lys Phe Ile Ala Gly Gln Ala Asn Val Glu Gly Trp Thr Pro Ser Thr
            20                  25                  30

aac aac tcg aac act gga atc ggc aac cac gga tct tgc tgc gcg gag      144
Asn Asn Ser Asn Thr Gly Ile Gly Asn His Gly Ser Cys Cys Ala Glu
        35                  40                  45

ctt gat atc tgg gaa gca aac agt atc tca gag gcc ttg act cct cac      192
Leu Asp Ile Trp Glu Ala Asn Ser Ile Ser Glu Ala Leu Thr Pro His
     50                  55                  60

cct tgc gat aca ccc ggc cta act gtt tgc act gct gat gac tgt ggt      240
Pro Cys Asp Thr Pro Gly Leu Thr Val Cys Thr Ala Asp Asp Cys Gly
 65                  70                  75                  80

ggt acc tac agc tcc aat cgt tat gcc ggt act tgc gac ccc gat          285
Gly Thr Tyr Ser Ser Asn Arg Tyr Ala Gly Thr Cys Asp Pro Asp
                 85                  90                  95


<210> SEQ ID NO 6
<211> LENGTH: 95
<212> TYPE: PRT
<213> ORGANISM: Penicillium funiculosum

<400> SEQUENCE: 6

Ala Lys Tyr Gly Thr Gly Tyr Cys Asp Ser Gln Cys Pro Arg Asp Leu
 1               5                  10                  15

Lys Phe Ile Ala Gly Gln Ala Asn Val Glu Gly Trp Thr Pro Ser Thr
            20                  25                  30

Asn Asn Ser Asn Thr Gly Ile Gly Asn His Gly Ser Cys Cys Ala Glu
        35                  40                  45

Leu Asp Ile Trp Glu Ala Asn Ser Ile Ser Glu Ala Leu Thr Pro His
    50                  55                  60

Pro Cys Asp Thr Pro Gly Leu Thr Val Cys Thr Ala Asp Asp Cys Gly
65                  70                  75                  80

Gly Thr Tyr Ser Ser Asn Arg Tyr Ala Gly Thr Cys Asp Pro Asp
                85                  90                  95


<210> SEQ ID NO 7
<211> LENGTH: 168
<212> TYPE: DNA
<213> ORGANISM: Penicillium funiculosum
<220> FEATURE:
<221> NAME/KEY: CDS
<222> LOCATION: (1)...(168)
<221> NAME/KEY: primer_bind
<222> LOCATION: (1)...(18)
<221> NAME/KEY: primer_bind
<222> LOCATION: (148)...(168)

<400> SEQUENCE: 7

ccg ggt act caa cct gtg gca tac tac gga cag cat ggt gtg agt gat       48
Pro Gly Thr Gln Pro Val Ala Tyr Tyr Gly Gln His Gly Val Ser Asp
```

-continued

```
 1               5                   10                  15

acg gta ctg cct ttc tca ttg gga gaa ggg att agg gat acg ttt gtc       96
Thr Val Leu Pro Phe Ser Leu Gly Glu Gly Ile Arg Asp Thr Phe Val
             20                  25                  30

aag gat gat cat tgt aca ccg aca aac ccg ccc gcc cct gct gct gga      144
Lys Asp Asp His Cys Thr Pro Thr Asn Pro Pro Ala Pro Ala Ala Gly
         35                  40                  45

agt gga acc cac atc aag tat gta                                      168
Ser Gly Thr His Ile Lys Tyr Val
     50                  55


<210> SEQ ID NO 8
<211> LENGTH: 56
<212> TYPE: PRT
<213> ORGANISM: Penicillium funiculosum

<400> SEQUENCE: 8

Pro Gly Thr Gln Pro Val Ala Tyr Tyr Gly Gln His Gly Val Ser Asp
 1               5                   10                  15

Thr Val Leu Pro Phe Ser Leu Gly Glu Gly Ile Arg Asp Thr Phe Val
             20                  25                  30

Lys Asp Asp His Cys Thr Pro Thr Asn Pro Pro Ala Pro Ala Ala Gly
         35                  40                  45

Ser Gly Thr His Ile Lys Tyr Val
    50                   55


<210> SEQ ID NO 9
<211> LENGTH: 349
<212> TYPE: PRT
<213> ORGANISM: Penicillium funiculosum
<220> FEATURE:
<221> NAME/KEY: SIGNAL
<222> LOCATION: (1)...(18)
<221> NAME/KEY: DOMAIN
<222> LOCATION: (19)...(294)
<223> OTHER INFORMATION: Catalytic
<221> NAME/KEY: ACT_SITE
<222> LOCATION: (134)...(138)
<223> OTHER INFORMATION: Putative
<221> NAME/KEY: CHAIN
<222> LOCATION: (295)...(314)
<221> NAME/KEY: BINDING
<222> LOCATION: (315)...(353)

<400> SEQUENCE: 9

Met Ala Ile Pro Leu Val Leu Val Leu Ala Trp Leu Leu Pro Val Val
            -15                 -10                  -5

Leu Ser Leu Thr Gln Val Asn Asn Phe Gly Asp Asn Pro Gly Ser Leu
         1               5                   10

Gln Met Tyr Ile Tyr Val Pro Asn Lys Leu Ala Ser Lys Pro Ala Ile
15                  20                  25                  30

Ile Val His Pro Cys Gly Gly Ser Ala Thr Glu Tyr Tyr Gly Met Tyr
                35                  40                  45

Asp Tyr His Ser Pro Ala Asp Gln Tyr Gly Tyr Ile Leu Ile Tyr Pro
            50                  55                  60

Ser Ala Thr Arg Asp Tyr Asn Cys Phe Asp Ala Tyr Ser Ser Ala Ser
        65                  70                  75

Leu Thr His Asn Gly Gly Ser Asp Ser Leu Ser Ile Val Asn Met Val
    80                  85                  90

Lys Tyr Val Ile Ser Thr Tyr Gly Ala Asp Ser Ser Lys Val Tyr Met
95                  100                 105                 110
```

-continued

```
Thr Gly Ser Ser Ser Gly Ala Ile Met Thr Asn Val Leu Ala Gly Ala
                115                 120                 125

Tyr Pro Asp Val Phe Ala Ala Gly Ser Ala Phe Ser Gly Met Pro Tyr
            130                 135                 140

Ala Cys Leu Tyr Gly Ala Gly Ala Ala Asp Pro Ile Met Ser Asn Gln
        145                 150                 155

Thr Cys Ser Gln Gly Gln Ile Gln His Thr Gly Gln Gln Trp Ala Ala
    160                 165                 170

Tyr Val His Asn Gly Tyr Pro Gly Tyr Thr Gly Gln Tyr Pro Arg Leu
175                 180                 185                 190

Gln Met Trp His Gly Thr Ala Asp Asn Val Ile Ser Tyr Ala Asp Leu
                195                 200                 205

Gly Gln Glu Ile Ser Gln Trp Thr Thr Ile Met Gly Leu Ser Phe Thr
            210                 215                 220

Gly Asn Gln Thr Asn Thr Pro Leu Ser Gly Tyr Thr Lys Met Val Tyr
        225                 230                 235

Gly Asp Gly Ser Lys Phe Gln Ala Tyr Ser Ala Ala Gly Val Gly His
    240                 245                 250

Phe Val Pro Thr Asp Val Ser Val Val Leu Asp Trp Phe Gly Ile Thr
255                 260                 265                 270

Ser Gly Thr Thr Thr Thr Thr Thr Pro Thr Thr Thr Pro Thr Thr Ser
                275                 280                 285

Thr Ser Pro Ser Ser Thr Gly Gly Cys Thr Ala Ala His Trp Ala Gln
            290                 295                 300

Cys Gly Gly Ile Gly Tyr Ser Gly Cys Thr Ala Cys Ala Ser Pro Tyr
        305                 310                 315

Thr Cys Gln Lys Ala Asn Asp Tyr Tyr Ser Gln Cys Leu
    320                 325                 330


<210> SEQ ID NO 10
<211> LENGTH: 10
<212> TYPE: PRT
<213> ORGANISM: Penicillium funiculosum

<400> SEQUENCE: 10

Ala Glu Ala Ile Asn Tyr Asn Gln Asp Tyr
 1               5                  10


<210> SEQ ID NO 11
<211> LENGTH: 14
<212> TYPE: PRT
<213> ORGANISM: Penicillium funiculosum

<400> SEQUENCE: 11

Gln Tyr Thr Leu Thr Leu Pro Ser Asn Tyr Asn Pro Asn Lys
 1               5                  10


<210> SEQ ID NO 12
<211> LENGTH: 10
<212> TYPE: PRT
<213> ORGANISM: Penicillium funiculosum

<400> SEQUENCE: 12

Ala Val Ala Val Met Ser Gly Ala Asn Leu
 1               5                  10


<210> SEQ ID NO 13
<211> LENGTH: 22
<212> TYPE: PRT
```

-continued

```
<213> ORGANISM: Penicillium funiculosum
<220> FEATURE:
<221> NAME/KEY: UNSURE
<222> LOCATION: (6)...(6)
<223> OTHER INFORMATION: Cys or Ala

<400> SEQUENCE: 13

Thr Glu Tyr Ser Gly Xaa Ala Ala Asp Ser Glu His Pro Val Trp Trp
 1               5                  10                  15

Ile Ala Phe Asp Gly Pro
            20


<210> SEQ ID NO 14
<211> LENGTH: 28
<212> TYPE: PRT
<213> ORGANISM: Pennicilium funiculosum

<400> SEQUENCE: 14

Asp Thr Phe Val Lys Asp Asp His Cys Thr Pro Thr Asn Pro Pro Ala
 1               5                  10                  15

Pro Ala Ala Gly Ser Gly Thr His Ile Lys Tyr Val
            20                  25
```

What is claimed is:

1. A *Penicillium funiculosum* strain IMI 378536 culture supernatant, wherein the supernatant improves feed digestibility when added to the feed as compared to the feed not having the supernatant.

2. The supernatant of claim 1, wherein said supernatant has xylanase activity, and wherein optimal xylanase activity is achieved at a pH between pH 3.0 and 5.0.

3. The supernatant of claim 1 comprising xylanases, β-glucanases, cellulases and feruloyl esterases.

4. The supernatant of claim 3 wherein the ratio between xylanases and β-glucanases/cellulases is between 10:1 and 1:4.

5. A method for improving the digestibility of farm animal feed which comprises treating the feed with the supernatant of claims 1, 2, 3, or 4, wherein the digestibility of the feed is improved when compared to the feed not treated with the supernatant.

6. The method of claim 5 wherein the farm animal is selected from the group consisting of poultry, swine and ruminants.

7. The method of claim 5 wherein the feed comprises cereal.

8. The method of claim 5 wherein the feed comprises oil seeds.

9. The method of claim 5 wherein the feed comprises a cereal by-product.

10. The method of claim 7 wherein the cereal is selected from the group consisting of wheat, barley, rye, triticale, oat, and rice.

11. The method of claim 8 wherein the oil seeds are selected from the group consisting of soya, sunflower, and rapeseed.

12. The method of claim 9 wherein the cereal by-product is wheat bran.

13. An enzyme mixture which improves feed digestibility when added to the feed as compared to the feed not having the enzyme mixture, wherein said enzyme mixture is prepared by the process comprising:

(a) growing a culture of *Penicillium funiculosum* strain IMI 378536; and (b) obtaining a supernatant from the culture, wherein the supernatant includes the enzyme mixture.

14. The enzyme mixture of claim 13, wherein said enzyme mixture comprises xylanase, and wherein optimal xylanase activity is achieved at a pH between pH 3.0 and 5.0.

15. The enzyme mixture of claim 13, comprising xylanases, β-glucanases, cellulases and feruloyl esterases.

16. The enzyme mixture of claim 15 wherein the ratio between xylanases and β-glucanases/cellulases is between 10:1 and 1:4.

17. An enzyme mixture comprising xylanases, β-glucanases, cellulases and feruloyl esterases, wherein optimal activity of the xylanases is achieved at a pH between pH 3.0 and 5.0, and wherein the enzyme mixture improves feed digestibility when added to feed as compared to the feed not having the enzyme mixture.

18. The enzyme mixture of claim 17, wherein the ratio between xylanases and β-glucanases/cellulases is between 10:1 and 1:4.

* * * * *

UNITED STATES PATENT AND TRADEMARK OFFICE

CERTIFICATE OF CORRECTION

PATENT NO. : 6,534,101 B1
DATED : March 18, 2003
INVENTOR(S) : Sabatier et al.

It is certified that error appears in the above-identified patent and that said Letters Patent is hereby corrected as shown below:

<u>Title page,</u>
Item [30], Foreign Application Priority Data, "Sep. 19, 2001" should read -- May 6, 1998 --
Item [56], References Cited, OTHER PUBLICATIONS,
Lachke et al., "hypercelulolytic" should read -- hypercellulolytic --; and
Ralet et al., "*Carbohyrate*" should read -- *Carbohydrate* --
Item [73], Assignee, "Aveatis" should read -- Aventis --; "Anthony" should read -- Antony --; "Aventis Animal Nutrition S.A., Antony (FR)" should read -- Aventis Animal Nutrition S.A., Antony (FR); and Rhodia Food, Courbevois (FR) --

<u>Column 1,</u>
Line 17, "breakdown" should read -- break down --
Line 33, "teed" should read -- feed --
Line 36, "Feed." should read -- feed. --
Line 44, "differents" should read -- different --

<u>Column 2,</u>
Lines 5-6, "Bacillus, Streptomyces, Saccharomyces, Schizosaccharomyces, Aspergillus." should read -- *Bacillus, Streptomyces, Saccharomyces, Schizosaccharomyces, Aspergillus.* --
Line 17, "increase" should read -- increases --
Line 44, "aminoacids" should read -- amino acids --
Line 64, "$\beta$-irradiations" should read -- $\beta$-irradiation --
Line 65, "medium." should read -- media. --

<u>Column 4,</u>
Line 35, "0,005%-0,35%" should read -- 0.005%-0.35% --
Line 36, "preferentially" should be indented
Line 36, "0,01%-0,25%" should read -- 0.01%-0.25% --
Line 38, "more preferably" should be indented
Line 42, "Antimicrobial" should read -- Antimicrobials --

<u>Column 5,</u>
Line 61, "extenction" should read -- extinction --

<u>Column 6,</u>
Lines 28 and 58, "endo-" should read -- Endo- --

<u>Column 7,</u>
Line 9, "transfered" should read -- transferred --

UNITED STATES PATENT AND TRADEMARK OFFICE

CERTIFICATE OF CORRECTION

PATENT NO. : 6,534,101 B1
DATED : March 18, 2003
INVENTOR(S) : Sabatier et al.

It is certified that error appears in the above-identified patent and that said Letters Patent is hereby corrected as shown below:

Column 8,
Lines 11 and 41, "endo-" should read -- Endo- --

Column 9,
Line 1, "($\Delta$Fr.min$^{-1}$)" should read -- ($\Delta F_r$.min$^{-1}$) --
Lines 22 and 47, "extenction" should read -- extinction --
Line 61, "-xyfopyranose" should read -- -xylopyranose --
Lines 63-64, "spectophotometrically" should read -- spectrophotometrically --

Column 10,
Line 10: "spectophotometrically" should read -- spectrophotometrically --
Line 61, "Elctrophoresis" should read -- Electrophoresis --
Line 63, "out standard" should read -- out using standard --

Column 13,
Line 1, "Phamacia" should read -- Pharmacia --
Line 9, 11 and 19, "$NH_4)_2SO_4$" should read -- $(NH_4)_2SO_4$ --
Line 20, "10 000×g" should read -- 10,000×g --
Line 27, "(NaCl (0–1M)" should read -- (NaCl 0–1M) --

Column 14,
Line 17, "occured" should read -- occurred --
Line 22, "deslated" should read -- desalted --
Line 29, "SDS-PGE" should read -- SDS-PAGE --
Line 31, "xyalanase" should read -- xylanase --

Column 17,
Line 4, "fuctions" should read -- functions --
Line 5, "be" should be deleted
Line 7, "differencies" should read -- differences --
Line 37, "pb" should read -- bp --

Column 18,
Line 6, "aproximatively" should read -- approximately --
Line 20, "35.450 Da" should read -- 35,450 Da --
Line 41, "Feruloy" should read -- Feruloyl --
Line 64, "Estease" should read -- Esterase --

UNITED STATES PATENT AND TRADEMARK OFFICE

CERTIFICATE OF CORRECTION

PATENT NO. : 6,534,101 B1
DATED : March 18, 2003
INVENTOR(S) : Sabatier et al.

It is certified that error appears in the above-identified patent and that said Letters Patent is hereby corrected as shown below:

Column 19,
Line 33, "degenate" should read -- degenerate --
Line 48, "(SEQ ID )" should be deleted
Line 49, "and" should be deleted
Line 51, "SEQ ID NO. 9" should read -- (SEQ ID NO: 9) --
Line 60, "S1361" should read -- S136 --
Line 61, "D2201" should read -- D220 --

Column 20,
Lines 27 and 28 "estease" should read -- esterase --

Column 22,
Line 61, "freezed;" should read -- frozen; --
Lines 62 and 63, "freezed," should read -- frozen, --

Column 23,
Line 6, "i" should be deleted
Line 41, "is" should read -- are --

Column 24,
Line 6, "polysaccharides's" should read -- polysaccharides --

Column 26,
Line 61, "freezed;" should read -- frozen; --
Lines 62 and 63, "freezed," should read -- frozen, --

Column 29,
Line 53, "fedstuffs" should read -- feedstuffs --

Column 30,
Line 5, "particules" should read -- particles --
Line 12, "spraid" should read -- sprayed --
Line 19, "serie" should read -- series --
Table 5.1, "29,5" should read -- 29.5 --;
"53,7" should read -- 53.7 --;
"57,8" should read -- 57.8 --;
"39,5" should read -- 39.5 --;
"43,1" should read -- 43.1 --;
"43,7" should read -- 43.7 --;
"47,7" should read -- 47.7 --; and
"0,08" (both occurrences) should read -- 0.08 --
Table 5.2, "," (comma) all occurrences should read -- . --(decimal point)

UNITED STATES PATENT AND TRADEMARK OFFICE

CERTIFICATE OF CORRECTION

PATENT NO. : 6,534,101 B1
DATED : March 18, 2003
INVENTOR(S) : Sabatier et al.

It is certified that error appears in the above-identified patent and that said Letters Patent is hereby corrected as shown below:

Column 32,
Table 6.1 (fn), "Vitamine" should read -- Vitamin --; and "Pantotenate" should read -- Pantothenate --

Column 33,
Table 6.3, row heading "Treatment" should be aligned with row 5; and row heading "Effect (P)" should be aligned with row 6
Table 6.4 (fn), "Overall" should read -- Overall[3] --

Column 34,
Table 6.5 (fn), "Overall" should read -- Overall[3] --
Line 44, "reproductibility" should read -- reproducibility --

Column 35,
SEQUENCE LISTING, "Pennicilium" should read -- Penicillium --

Column 41,
SEQUENCE LISTING, "Pennicium" should read -- Penicillium --

Column 47,
SEQUENCE LISTING, "Pennicilium" should read -- Penicillium --

Column 48,
Line 49, "An" should read -- The --; and "mixture" should read -- mixture of claim 13 --

Signed and Sealed this

Seventh Day of October, 2003

JAMES E. ROGAN
*Director of the United States Patent and Trademark Office*

UNITED STATES PATENT AND TRADEMARK OFFICE

CERTIFICATE OF CORRECTION

PATENT NO. : 6,534,101 B1
APPLICATION NO. : 09/462246
DATED : March 18, 2003
INVENTOR(S) : Sabatier et al.

It is certified that error appears in the above-identified patent and that said Letters Patent is hereby corrected as shown below:

ON THE TITLE PAGE:

Item (30) Foreign Application Priority Data:

should read -- May 06, 1998 -- instead of "Sep. 19, 2001"

Signed and Sealed this

Twenty-eighth Day of October, 2008

JON W. DUDAS
*Director of the United States Patent and Trademark Office*